US012664870B2

(12) United States Patent
Turiello

(10) Patent No.: US 12,664,870 B2
(45) Date of Patent: *Jun. 23, 2026

(54) METHOD, DEVICE AND SYSTEM OF A SENSOR INTEGRATED COMPUTING PLATFORM OF A FIREFIGHTER AIR REPLENISHMENT SYSTEM FOR REMOTE MONITORING AND ACCESS THEREOF

(71) Applicant: RESCUE AIR SYSTEMS, INC., San Carlos, CA (US)

(72) Inventor: Anthony J. Turiello, Westlake, TX (US)

(73) Assignee: Rescue Air Systems, Inc., San Carlos, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 18/197,114

(22) Filed: May 15, 2023

(65) Prior Publication Data

US 2024/0001178 A1     Jan. 4, 2024

Related U.S. Application Data

(60) Provisional application No. 63/359,882, filed on Jul. 11, 2022, provisional application No. 63/356,996, filed on Jun. 29, 2022.

(51) Int. Cl.
*G08B 21/18*       (2006.01)
*G01N 33/00*       (2006.01)
G08B 21/02         (2006.01)

(52) U.S. Cl.
CPC ....... *G08B 21/182* (2013.01); *G01N 33/0031* (2013.01); *G08B 21/02* (2013.01)

(58) Field of Classification Search
CPC . A62C 3/0207; A62C 99/0009; B05B 7/2491; G08B 21/182; G08B 21/02; G01N 33/0031; A62B 15/00
See application file for complete search history.

(56) References Cited

U.S. PATENT DOCUMENTS 1,040,311  A     10/1912  Halloran
1,643,155  A      9/1927  Eisenschitz
(Continued)

FOREIGN PATENT DOCUMENTS

AR            070623 A1     4/2010
AU        2019101454 A4     1/2020
(Continued)

OTHER PUBLICATIONS

"Influence of Internal Gas Pipelines Built into the Structure on the Safety of Residents and Energy Eficiency Factors of the Buildings", Published at Latvian Journal of Physics and Technical Sciences, Published on [Oct. 2022] http://surl.li/fdzun.
(Continued)

*Primary Examiner* — Mirza F Alam
(74) *Attorney, Agent, or Firm* — Foley & Lardner LLP

(57)     ABSTRACT

Disclosed are a method, a device and a system of a sensor integrated safety system based computing platform. The computing platform is executed on a data processing device and integrated with a set of sensors associated with components of a safety system In accordance therewith, the data processing device collects a number of parameters of the components of the safety system and/or of access thereof through detection of the number of parameters via the set of sensors. The number of parameters includes one or more parameter(s) related to breathable air from a source within the safety system supplied thereacross via a fixed piping system implemented therein and/or access of the breathable air. The data processing device also monitors the safety system and/or one or more components thereof based on the collected number of parameters.

20 Claims, 9 Drawing Sheets

(56) References Cited

U.S. PATENT DOCUMENTS

| | | | |
|---|---|---|---|
| 2,341,113 A | 2/1944 | Nelson | |
| 3,429,186 A | 2/1969 | Price | |
| 3,477,688 A | 11/1969 | Cruse | |
| 3,625,065 A | 12/1971 | Thompson | |
| 3,925,763 A | 12/1975 | Wadhwani et al. | |
| 4,014,216 A | 3/1977 | Thornton | |
| 4,023,146 A | 5/1977 | Carroll | |
| 4,091,874 A | 5/1978 | Monma | |
| 4,134,457 A | 1/1979 | Raymond | |
| 4,165,738 A | 8/1979 | Dyer | |
| 4,336,590 A | 6/1982 | Jacq | |
| 4,373,522 A | 2/1983 | Zien | |
| 4,375,637 A | 3/1983 | Desjardins | |
| 4,380,187 A | 4/1983 | Wicks | |
| 4,413,622 A | 11/1983 | Austin | |
| 4,467,796 A | 8/1984 | Beagley | |
| 4,570,719 A | 2/1986 | Wilk | |
| 4,856,565 A | 8/1989 | Schoeffl et al. | |
| 4,862,931 A | 9/1989 | Vella | |
| 4,905,684 A | 3/1990 | Heffer | |
| 5,095,899 A | 3/1992 | Green | |
| 5,163,422 A | 11/1992 | Burgess | |
| 5,396,885 A | 3/1995 | Nelson | |
| 5,497,855 A | 3/1996 | Moore | |
| 5,507,283 A | 4/1996 | Grivas | |
| 5,538,690 A | 7/1996 | Greer et al. | |
| 5,564,626 A | 10/1996 | Kettler et al. | |
| 5,570,685 A | 11/1996 | Turiello | |
| 5,619,333 A | 4/1997 | Staff et al. | |
| 5,707,005 A | 1/1998 | Kettler et al. | |
| 5,720,659 A | 2/1998 | Wicks | |
| 5,730,121 A | 3/1998 | Hawkins et al. | |
| 5,746,976 A | 5/1998 | Yamada et al. | |
| 5,800,260 A | 9/1998 | Kao | |
| 5,901,758 A | 5/1999 | Hwang et al. | |
| 5,979,440 A | 11/1999 | Honkonen et al. | |
| 5,992,532 A | 11/1999 | Ramsey et al. | |
| 6,112,807 A | 9/2000 | Dage | |
| 6,310,552 B1 | 10/2001 | Stumberg et al. | |
| 6,357,532 B1 | 3/2002 | Laskaris et al. | |
| 6,369,716 B1 | 4/2002 | Abbas et al. | |
| 6,401,487 B1 | 6/2002 | Kotliar | |
| 6,418,752 B2 | 7/2002 | Kotliar | |
| 6,488,026 B2 | 12/2002 | Lauer | |
| 6,502,421 B2 | 1/2003 | Kotliar | |
| 6,543,444 B1 | 4/2003 | Lewis | |
| 6,585,583 B1 | 7/2003 | Chan | |
| 6,647,301 B1 | 11/2003 | Sederlund et al. | |
| 6,712,071 B1 | 3/2004 | Parker | |
| 6,810,910 B2 | 11/2004 | McHugh | |
| 6,832,952 B2 | 12/2004 | Faltesek et al. | |
| 6,866,102 B2 | 3/2005 | Boyce et al. | |
| 6,873,256 B2 | 3/2005 | Pedersen et al. | |
| 6,920,874 B1 | 7/2005 | Siegel | |
| 6,940,403 B2 | 9/2005 | Kail et al. | |
| 6,999,562 B2 | 2/2006 | Winick | |
| 7,091,852 B2 | 8/2006 | Mason et al. | |
| 7,100,689 B2 | 9/2006 | Williams et al. | |
| 7,124,833 B2 | 10/2006 | Sant'Angelo | |
| 7,161,481 B2 | 1/2007 | Turner | |
| 7,168,428 B1 | 1/2007 | Zoha | |
| 7,183,115 B1 | 2/2007 | Lauglin | |
| 7,186,084 B2 | 3/2007 | Bunker et al. | |
| 7,204,249 B1 | 4/2007 | Richey et al. | |
| 7,221,260 B2 | 5/2007 | Berezowski et al. | |
| 7,250,000 B2 | 7/2007 | Daniels | |
| 7,255,104 B2 | 8/2007 | Phillips | |
| 7,302,313 B2 | 11/2007 | Sharp et al. | |
| 7,347,204 B1 * | 3/2008 | Lindsey | A62B 7/02 |
| | | | 128/202.13 |
| 7,377,835 B2 | 5/2008 | Parkulo et al. | |
| 7,395,704 B2 | 7/2008 | DiFoggio | |
| 7,468,082 B2 | 12/2008 | Gordon | |
| 7,509,968 B2 | 3/2009 | Surawski | |
| 7,527,056 B2 | 5/2009 | Turiello | |
| 7,548,833 B2 | 6/2009 | Ahmed | |
| 7,568,375 B2 | 8/2009 | Sasaki et al. | |
| 7,598,856 B1 | 10/2009 | Nick et al. | |
| 7,621,269 B2 | 11/2009 | Turiello | |
| 7,654,279 B2 | 2/2010 | Horton et al. | |
| 7,658,190 B1 | 2/2010 | Phifer et al. | |
| 7,673,629 B2 | 3/2010 | Turiello | |
| 7,677,247 B2 | 3/2010 | Turiello | |
| 7,694,678 B2 | 4/2010 | Turiello | |
| 7,710,282 B1 | 5/2010 | Young | |
| 7,765,072 B2 | 7/2010 | Eller et al. | |
| 7,770,610 B2 | 8/2010 | Lisle | |
| 7,804,402 B2 | 9/2010 | Lang et al. | |
| 7,817,050 B2 | 10/2010 | Goodman et al. | |
| 7,823,609 B2 | 11/2010 | Wonders | |
| 7,857,068 B2 | 12/2010 | Wagner | |
| 7,868,752 B1 | 1/2011 | Herbold | |
| 7,880,607 B2 | 2/2011 | Olson et al. | |
| 7,921,869 B2 | 4/2011 | Surawski | |
| 7,934,411 B2 | 5/2011 | Koch | |
| 7,953,228 B2 | 5/2011 | Faltesek et al. | |
| 7,975,729 B2 | 7/2011 | Lisle | |
| 8,038,948 B1 | 10/2011 | Laughlin | |
| 8,074,278 B2 | 12/2011 | Law et al. | |
| 8,114,954 B2 | 2/2012 | DeBruin | |
| 8,116,913 B2 | 2/2012 | Mirpourian et al. | |
| 8,147,302 B2 | 4/2012 | Desrochers et al. | |
| 8,149,109 B2 | 4/2012 | Lontka | |
| 8,196,479 B2 | 6/2012 | Ludwick et al. | |
| 8,219,249 B2 | 7/2012 | Harrod et al. | |
| 8,291,941 B1 | 10/2012 | Berardi | |
| 8,371,295 B2 | 2/2013 | Turiello | |
| 8,375,876 B2 | 2/2013 | Van Tassel | |
| 8,375,948 B2 | 2/2013 | Turiello | |
| 8,381,726 B2 | 2/2013 | Turiello | |
| 8,413,653 B2 | 4/2013 | Turiello | |
| 8,443,800 B2 | 5/2013 | Turiello | |
| 8,517,696 B2 | 8/2013 | McLoughlin et al. | |
| 8,538,687 B2 | 9/2013 | Plocher et al. | |
| 8,573,317 B2 | 11/2013 | Krüger et al. | |
| 8,602,119 B2 | 12/2013 | Wagner | |
| 8,611,323 B2 | 12/2013 | Berger et al. | |
| 8,668,023 B2 | 3/2014 | Wilkins et al. | |
| 8,701,718 B1 | 4/2014 | Turiello | |
| 8,733,355 B2 | 5/2014 | Turiello | |
| 8,745,792 B2 | 6/2014 | McGlynn | |
| 8,755,839 B2 | 6/2014 | Parkulo et al. | |
| 8,770,190 B2 | 7/2014 | Doherty et al. | |
| 8,773,946 B2 | 7/2014 | Padmanabhan et al. | |
| 8,795,041 B2 | 8/2014 | Saito et al. | |
| 8,797,141 B2 | 8/2014 | Best et al. | |
| 8,797,210 B2 | 8/2014 | Derrick et al. | |
| 8,866,618 B2 | 10/2014 | Cotten et al. | |
| 8,995,946 B2 | 3/2015 | Miller | |
| 9,010,019 B2 | 4/2015 | Mittelmark | |
| 9,032,994 B2 | 5/2015 | McHugh et al. | |
| 9,033,061 B2 | 5/2015 | Chattaway et al. | |
| 9,105,171 B2 | 8/2015 | Flood et al. | |
| 9,109,981 B2 | 8/2015 | Sharp | |
| 9,134,284 B1 | 9/2015 | Laughlin | |
| 9,175,975 B2 | 11/2015 | Shtukater | |
| 9,220,937 B2 | 12/2015 | Wagner | |
| 9,234,661 B2 | 1/2016 | Young et al. | |
| 9,235,975 B2 | 1/2016 | Gettings et al. | |
| 9,242,126 B2 | 1/2016 | Turiello | |
| 9,243,753 B2 | 1/2016 | Wonders | |
| 9,328,936 B2 | 5/2016 | Meirav et al. | |
| 9,347,677 B2 | 5/2016 | Eberlein et al. | |
| 9,404,666 B2 | 8/2016 | Terlson et al. | |
| 9,466,199 B2 | 10/2016 | McNabb et al. | |
| 9,468,157 B2 | 10/2016 | Hu | |
| 9,564,028 B2 | 2/2017 | Cerrano | |
| 9,566,608 B2 | 2/2017 | Tran | |
| 9,670,670 B2 | 6/2017 | Teron | |
| 9,671,794 B1 | 6/2017 | Lymberopoulos et al. | |
| 9,682,257 B2 | 6/2017 | Zhao et al. | |
| 9,702,802 B2 | 7/2017 | Ajay et al. | |
| 9,724,484 B2 | 8/2017 | Robey | |
| 9,733,149 B2 | 8/2017 | Eberlein | |

(56) References Cited

U.S. PATENT DOCUMENTS

| | | |
|---|---|---|
| 9,829,895 B2 | 11/2017 | McLoughlin et al. |
| 9,852,604 B2 | 12/2017 | Poder |
| 9,875,631 B2 | 1/2018 | Mittleman et al. |
| 9,927,066 B1 | 3/2018 | Wonders |
| 9,933,115 B2 | 4/2018 | Rado et al. |
| 9,964,470 B2 | 5/2018 | Sharp |
| 10,042,164 B2 | 8/2018 | Kuutti et al. |
| 10,044,857 B2 | 8/2018 | Philbin |
| 10,052,509 B2 | 8/2018 | Wagner |
| 10,062,233 B1 | 8/2018 | Rogers et al. |
| 10,074,295 B2 | 9/2018 | Hyman |
| 10,078,865 B2 | 9/2018 | Joshi et al. |
| 10,121,361 B2 | 11/2018 | Delullis et al. |
| 10,124,196 B2 | 11/2018 | Roberts |
| 10,139,282 B2 | 11/2018 | Chrostowski |
| 10,156,320 B2 | 12/2018 | Toelle |
| 10,161,923 B1 | 12/2018 | Laughlin |
| 10,192,411 B2 | 1/2019 | Wedig et al. |
| 10,311,444 B1 | 6/2019 | Conboy |
| 10,380,862 B1 | 8/2019 | Heidary |
| 10,380,863 B2 | 8/2019 | Wedig et al. |
| 10,400,442 B2 | 9/2019 | Power et al. |
| 10,417,451 B2 | 9/2019 | Park et al. |
| 10,426,064 B2 | 9/2019 | Slessman et al. |
| 10,490,055 B2 | 11/2019 | Myllymäki |
| 10,503,180 B2 | 12/2019 | Blackley |
| 10,529,215 B2 | 1/2020 | Brown |
| 10,563,886 B2 | 2/2020 | McCormick et al. |
| 10,632,331 B2 | 4/2020 | Mele |
| 10,639,508 B2 | 5/2020 | Müller et al. |
| 10,738,943 B2 | 8/2020 | Tilhof |
| 10,787,803 B2 | 9/2020 | Leahy |
| 10,789,665 B2 | 9/2020 | Comello |
| 10,808,396 B2 | 10/2020 | Zhang et al. |
| 10,834,482 B2 | 11/2020 | Speicher et al. |
| 10,890,294 B2 | 1/2021 | Santos et al. |
| 10,901,373 B2 | 1/2021 | Locke et al. |
| 10,969,131 B2 | 4/2021 | Sinha et al. |
| 11,009,186 B2 | 5/2021 | Sung |
| 11,027,236 B2 | 6/2021 | Maayan et al. |
| 11,045,800 B1 | 6/2021 | Kaplan et al. |
| 11,055,973 B2 | 7/2021 | Wedig et al. |
| 11,070,390 B2 | 7/2021 | Park et al. |
| 11,111,767 B2 | 9/2021 | Anders |
| 11,135,461 B2 | 10/2021 | Beechy et al. |
| 11,162,181 B2 | 11/2021 | Harano et al. |
| 11,181,875 B2 | 11/2021 | Kummer et al. |
| 11,185,650 B2 | 11/2021 | Almqvist |
| 11,187,223 B2 | 11/2021 | Ward et al. |
| 11,191,222 B2 | 12/2021 | Cho et al. |
| 11,226,604 B2 | 1/2022 | Goyal |
| 11,238,187 B2 | 2/2022 | Nikolayev et al. |
| 11,391,474 B2 | 7/2022 | Eplee |
| 11,410,539 B2 | 8/2022 | Kasiviswanathan |
| 11,426,553 B2 | 8/2022 | Dube et al. |
| 11,439,856 B2 | 9/2022 | Laskaris et al. |
| 11,514,764 B2 | 11/2022 | Correnti et al. |
| 11,536,476 B2 | 12/2022 | Nesler et al. |
| 11,626,002 B2 | 4/2023 | Donegan et al. |
| 11,719,625 B2 | 8/2023 | Carras et al. |
| 11,768,138 B2 | 9/2023 | Jamison et al. |
| 11,810,216 B1 | 11/2023 | Foiles et al. |
| 11,964,269 B2 | 4/2024 | Kaplan et al. |
| 12,339,267 B2 | 6/2025 | Lazea et al. |
| 12,345,433 B2 | 7/2025 | Pham et al. |
| 12,411,118 B2 | 9/2025 | Mcmanus et al. |
| 2001/0032892 A1 | 10/2001 | Brooks et al. |
| 2002/0121381 A1 | 9/2002 | Reilly |
| 2002/0185283 A1 | 12/2002 | Taylor |
| 2003/0183300 A1 | 10/2003 | Siebert |
| 2004/0045350 A1 | 3/2004 | Jones et al. |
| 2005/0066711 A1 | 3/2005 | Discenzo |
| 2006/0005880 A1 | 1/2006 | Baker et al. |
| 2006/0173579 A1 | 8/2006 | Desrochers et al. |
| 2006/0173580 A1 | 8/2006 | Desrochers et al. |
| 2006/0196254 A1 | 9/2006 | Fjerdingstad et al. |
| 2006/0213513 A1 | 9/2006 | Seong |
| 2006/0234621 A1 | 10/2006 | Desrochers et al. |
| 2007/0017520 A1 | 1/2007 | Gale et al. |
| 2007/0163578 A1 | 7/2007 | Lisle |
| 2007/0175470 A1 | 8/2007 | Brookman et al. |
| 2008/0041377 A1 | 2/2008 | Turiello |
| 2008/0041378 A1 | 2/2008 | Turiello |
| 2008/0041379 A1 | 2/2008 | Turiello |
| 2008/0105443 A1 | 5/2008 | Molz et al. |
| 2008/0236846 A1 | 10/2008 | Gamble et al. |
| 2009/0058669 A1 | 3/2009 | Santos |
| 2009/0159365 A1 | 6/2009 | O'Brien |
| 2009/0178675 A1 | 7/2009 | Turiello |
| 2009/0283151 A1 | 11/2009 | Turiello |
| 2010/0031955 A1 | 2/2010 | Turiello |
| 2010/0032040 A1* | 2/2010 | Turiello ............... A62B 15/00 |
| | | 137/861 |
| 2010/0081411 A1 | 4/2010 | Montenero |
| 2010/0084043 A1 | 4/2010 | Turiello |
| 2010/0147297 A1 | 6/2010 | Brewer et al. |
| 2010/0154922 A1 | 6/2010 | Turiello |
| 2010/0201536 A1 | 8/2010 | Robertson et al. |
| 2011/0187524 A1 | 8/2011 | Cochran, III |
| 2011/0192479 A1 | 8/2011 | Yokota |
| 2011/0259198 A1* | 10/2011 | Kim ..................... B01D 46/62 |
| | | 96/397 |
| 2011/0259580 A1 | 10/2011 | Head |
| 2011/0277490 A1 | 11/2011 | Meirav |
| 2012/0031525 A1 | 2/2012 | Wonders |
| 2012/0266889 A1 | 10/2012 | Roberts |
| 2013/0033377 A1 | 2/2013 | Hoseit |
| 2013/0086933 A1 | 4/2013 | Holtkamp et al. |
| 2013/0087153 A1 | 4/2013 | Jung |
| 2013/0105010 A1 | 5/2013 | McLoughlin |
| 2014/0077110 A1 | 3/2014 | Gamard et al. |
| 2014/0188286 A1 | 7/2014 | Hunka |
| 2014/0232876 A1 | 8/2014 | Dougherty |
| 2014/0261406 A1 | 9/2014 | Fabian |
| 2014/0338927 A1 | 11/2014 | Palle |
| 2014/0349707 A1 | 11/2014 | Bang |
| 2015/0033765 A1 | 2/2015 | Blalock |
| 2015/0077737 A1 | 3/2015 | Belinsky et al. |
| 2015/0096768 A1 | 4/2015 | DuBrucq et al. |
| 2015/0130205 A1 | 5/2015 | Caskey |
| 2015/0131262 A1 | 5/2015 | Mabry |
| 2015/0170486 A1 | 6/2015 | Penland |
| 2015/0204484 A1 | 7/2015 | Modirzareh et al. |
| 2015/0217518 A1 | 8/2015 | Chun et al. |
| 2015/0330873 A1 | 11/2015 | Atchison |
| 2015/0369498 A1 | 12/2015 | Motomura et al. |
| 2016/0003524 A1 | 1/2016 | Blalock |
| 2016/0114196 A1 | 4/2016 | Tribble |
| 2016/0116181 A1 | 4/2016 | Aultman et al. |
| 2016/0133108 A1 | 5/2016 | Bucsa et al. |
| 2016/0136017 A1 | 5/2016 | Caskey |
| 2016/0138759 A1 | 5/2016 | Rado et al. |
| 2016/0197772 A1 | 7/2016 | Britt et al. |
| 2016/0334061 A1 | 11/2016 | Toelle |
| 2016/0343187 A1 | 11/2016 | Trani |
| 2017/0006107 A1 | 1/2017 | Dawes et al. |
| 2017/0084156 A1 | 3/2017 | Myllymäki |
| 2017/0122580 A1 | 5/2017 | Karamanos et al. |
| 2017/0180829 A1 | 6/2017 | Schwarzkopf et al. |
| 2017/0236397 A1 | 8/2017 | Myslenski |
| 2017/0303580 A1 | 10/2017 | Cameron et al. |
| 2017/0310498 A1 | 10/2017 | Brandman et al. |
| 2018/0181094 A1 | 6/2018 | Funk et al. |
| 2018/0197393 A1 | 7/2018 | Gallo et al. |
| 2018/0200552 A1 | 7/2018 | Wertsberger |
| 2018/0243591 A1 | 8/2018 | DeWitt |
| 2018/0283614 A1 | 10/2018 | Gandolfo |
| 2018/0363939 A1 | 12/2018 | Mccormick et al. |
| 2018/0375444 A1 | 12/2018 | Gamroth |
| 2019/0023529 A1 | 1/2019 | Lau |
| 2019/0103986 A1 | 4/2019 | Brandman et al. |
| 2019/0143161 A1 | 5/2019 | Burkhart et al. |
| 2019/0171780 A1 | 6/2019 | Santarone et al. |
| 2019/0174208 A1 | 6/2019 | Speicher et al. |

(56) References Cited

U.S. PATENT DOCUMENTS

| | | | |
|---|---|---|---|
| 2019/0203885 A1 | 7/2019 | Sung | |
| 2019/0277449 A1 | 9/2019 | Bourgeois et al. | |
| 2019/0282839 A1 | 9/2019 | Wenzel et al. | |
| 2020/0012307 A1 | 1/2020 | Scelzi | |
| 2020/0054905 A1 | 2/2020 | Livchak et al. | |
| 2020/0107475 A1 | 4/2020 | Keisling et al. | |
| 2020/0143300 A1 | 5/2020 | Weldemariam et al. | |
| 2020/0225313 A1 | 7/2020 | Coles | |
| 2020/0232309 A1 | 7/2020 | Deutch et al. | |
| 2020/0294372 A1 | 9/2020 | Rodriguez | |
| 2020/0334778 A1 | 10/2020 | Lotter | |
| 2020/0349661 A1 | 11/2020 | Dutta et al. | |
| 2021/0023323 A1 | 1/2021 | Wilkinson et al. | |
| 2021/0038926 A1 | 2/2021 | Reedy | |
| 2021/0113864 A1 | 4/2021 | Nam | |
| 2021/0183218 A1 | 6/2021 | Johnson et al. | |
| 2021/0237309 A1 | 8/2021 | Tessien | |
| 2021/0241595 A1 | 8/2021 | Young et al. | |
| 2021/0268322 A1 | 9/2021 | Thomas et al. | |
| 2021/0280034 A1 | 9/2021 | Wedig et al. | |
| 2021/0297336 A1 | 9/2021 | Ramakrishnaiah et al. | |
| 2021/0299495 A1 | 9/2021 | Feenstra | |
| 2021/0311008 A1 | 10/2021 | Hill | |
| 2021/0358238 A1 | 11/2021 | Rogers et al. | |
| 2021/0379429 A1* | 12/2021 | Darnell | B05B 7/2491 |
| 2022/0010996 A1 | 1/2022 | Carrieri | |
| 2022/0019186 A1 | 1/2022 | De Andrade et al. | |
| 2022/0099641 A1 | 3/2022 | Desrochers | |
| 2022/0103914 A1 | 3/2022 | Lotter | |
| 2022/0134147 A1 | 5/2022 | Webb et al. | |
| 2022/0233900 A1 | 7/2022 | Williams | |
| 2022/0260270 A1 | 8/2022 | Abate et al. | |
| 2022/0297110 A1 | 9/2022 | Kaplan et al. | |
| 2022/0404056 A1 | 12/2022 | Bloemer et al. | |
| 2023/0034481 A1 | 2/2023 | Benton et al. | |
| 2023/0070772 A1 | 3/2023 | Bingham et al. | |
| 2023/0173128 A1 | 6/2023 | Slotkin et al. | |
| 2023/0298346 A1 | 9/2023 | Alshammary | |
| 2023/0319241 A1 | 10/2023 | Turiello et al. | |
| 2024/0001161 A1 | 1/2024 | Turiello | |
| 2024/0001178 A1 | 1/2024 | Turiello | |
| 2024/0036537 A1* | 2/2024 | Gupta | H04L 12/2834 |
| 2025/0216034 A1 | 7/2025 | Despres et al. | |

FOREIGN PATENT DOCUMENTS

| | | |
|---|---|---|
| AU | 2021105506 A4 | 11/2021 |
| CA | 2760676 A1 | 11/2010 |
| CN | 101853549 A | 10/2010 |
| CN | 101968244 A | 2/2011 |
| CN | 201775882 U | 3/2011 |
| CN | 202052220 U | 11/2011 |
| CN | 202078672 U | 12/2011 |
| CN | 202615547 U | 12/2012 |
| CN | 102739786 B | 4/2013 |
| CN | 101298769 B1 | 8/2013 |
| CN | 203154649 U | 8/2013 |
| CN | 203160791 U | 8/2013 |
| CN | 203190560 U | 9/2013 |
| CN | 102364016 B | 2/2014 |
| CN | 102500021 B | 7/2014 |
| CN | 203799482 U | 8/2014 |
| CN | 102365458 B | 9/2014 |
| CN | 104056374 A | 9/2014 |
| CN | 104826248 A | 8/2015 |
| CN | 204534128 U | 8/2015 |
| CN | 104906717 A | 9/2015 |
| CN | 205031799 U | 2/2016 |
| CN | 104260763 B | 8/2016 |
| CN | 105917208 A | 8/2016 |
| CN | 106310553 A | 1/2017 |
| CN | 106899665 A | 6/2017 |
| CN | 105143778 B | 8/2017 |
| CN | 105247269 A | 9/2017 |
| CN | 206808757 U | 12/2017 |

| | | |
|---|---|---|
| CN | 107991999 A | 5/2018 |
| CN | 105892538 B | 8/2018 |
| CN | 207750720 U | 8/2018 |
| CN | 106546008 A | 9/2018 |
| CN | 105091097 B | 1/2019 |
| CN | 105547285 A | 1/2019 |
| CN | 208536257 U | 2/2019 |
| CN | 109859368 A | 6/2019 |
| CN | 109939387 A | 6/2019 |
| CN | 110469950 A | 11/2019 |
| CN | 110478804 A | 11/2019 |
| CN | 110494811 A | 11/2019 |
| CN | 110673739 A | 1/2020 |
| CN | 209926530 U | 1/2020 |
| CN | 210135667 U | 3/2020 |
| CN | 111210588 A | 5/2020 |
| CN | 210739978 U | 6/2020 |
| CN | 111544817 A | 8/2020 |
| CN | 110047240 B | 10/2020 |
| CN | 109404582 B | 11/2020 |
| CN | 112344484 A | 2/2021 |
| CN | 212491267 U | 2/2021 |
| CN | 112657081 A | 4/2021 |
| CN | 108295407 B | 5/2021 |
| CN | 111258251 A | 5/2021 |
| CN | 113365029 A | 9/2021 |
| CN | 110493568 B | 10/2021 |
| CN | 111243219 A | 11/2021 |
| CN | 214550694 U | 11/2021 |
| CN | 113769292 A | 12/2021 |
| CN | 113842716 A | 12/2021 |
| CN | 114146332 A | 3/2022 |
| CN | 114205385 A | 3/2022 |
| CN | 114235301 A | 3/2022 |
| CN | 106678991 B | 5/2022 |
| CN | 114613092 A | 6/2022 |
| CN | 216855578 U | 7/2022 |
| CN | 217526213 U | 10/2022 |
| CN | 115645769 A | 1/2023 |
| EP | 2320397 B1 | 5/2012 |
| EP | 2 151 263 B1 | 3/2014 |
| EP | 2 982 416 A1 | 2/2016 |
| EP | 2373384 B1 | 10/2018 |
| GB | 2248884 A | 4/1992 |
| JP | H06-343709 A | 12/1994 |
| JP | H08-124064 A | 5/1996 |
| JP | 3397382 B2 | 4/2003 |
| JP | 2004-298554 A | 10/2004 |
| JP | 2005291634 A | 10/2005 |
| JP | 5117700 B2 | 1/2013 |
| JP | 5654124 B2 | 1/2015 |
| JP | 5719010 B2 | 5/2015 |
| JP | 6189404 B2 | 8/2017 |
| JP | 6321134 B2 | 5/2018 |
| JP | 2021186616 A | 12/2021 |
| JP | 7109988 B2 | 8/2022 |
| KR | 20050097400 A | 10/2005 |
| KR | 100880023 B1 | 2/2009 |
| KR | 10-2010-0012689 A | 2/2010 |
| KR | 100945260 B1 | 3/2010 |
| KR | 10-2010-0115024 A | 10/2010 |
| KR | 101024944 B1 | 3/2011 |
| KR | 20110078600 A | 7/2011 |
| KR | 10-1088547 B1 | 11/2011 |
| KR | 20110002589 U | 11/2011 |
| KR | 101089513 B1 | 12/2011 |
| KR | 101208662 B1 | 12/2012 |
| KR | 20130017610 A | 8/2013 |
| KR | 101722045 B1 | 3/2017 |
| KR | 101747360 B1 | 6/2017 |
| KR | 101762550 B1 | 7/2017 |
| KR | 10-1840682 B1 | 10/2017 |
| KR | 101790694 B1 | 11/2017 |
| KR | 20170138810 A | 12/2017 |
| KR | 101815533 B1 | 1/2018 |
| KR | 101841954 B1 | 3/2018 |
| KR | 101845263 B1 | 4/2018 |
| KR | 101845264 B1 | 5/2018 |
| KR | 101859878 B1 | 5/2018 |

(56) References Cited

FOREIGN PATENT DOCUMENTS

| KR | 101859955 B1 | 5/2018 |
|---|---|---|
| KR | 101887164 B1 | 9/2018 |
| KR | 101902976 B1 | 10/2018 |
| KR | 10-2019-0043669 A | 4/2019 |
| KR | 20180001140 U | 6/2019 |
| KR | 101996949 B1 | 7/2019 |
| KR | 102008625 B1 | 8/2019 |
| KR | 101994222 B1 | 9/2019 |
| KR | 102035835 B1 | 10/2019 |
| KR | 10-2019-0131158 A | 11/2019 |
| KR | 102050539 B1 | 12/2019 |
| KR | 10-2020-0027390 A | 3/2020 |
| KR | 102169547 B1 | 10/2020 |
| KR | 102263178 B1 | 6/2021 |
| KR | 102277919 B1 | 7/2021 |
| KR | 102300167 B1 | 9/2021 |
| KR | 102355909 B1 | 2/2022 |
| KR | 20220056659 A | 5/2022 |
| NL | 2019479 B1 | 8/2018 |
| RU | 74076 U | 6/2008 |
| RU | 2465933 C2 | 11/2012 |
| RU | 2717525 C1 | 3/2020 |
| RU | 2724093 C1 | 6/2020 |
| TW | 201425832 A | 9/2015 |
| TW | M540352 U | 4/2017 |
| WO | 2003031892 A1 | 4/2003 |
| WO | 2006047246 A2 | 5/2006 |
| WO | 2008021538 A2 | 2/2008 |
| WO | 2010063266 A1 | 6/2010 |
| WO | 2011034334 A2 | 3/2011 |
| WO | 2014208865 A1 | 12/2014 |
| WO | 2016205053 A1 | 12/2016 |
| WO | 2018038434 A1 | 3/2018 |
| WO | 2018176196 A1 | 10/2018 |
| WO | 2018236571 A1 | 12/2018 |
| WO | WO-2021/250389 A1 | 12/2021 |
| WO | 2022066099 A1 | 3/2022 |
| WO | 2023000087 A1 | 1/2023 |

OTHER PUBLICATIONS

"Indoor air quality in green buildings: A case-study in a residential high-rise building in the northeastern United States", Published at Journal of Environmental Science and Health, Published on [Feb. 2015] http://surl.li/fdzxk.

"Indoor Air-Quality Data-Monitoring System: Long-Term Monitoring Benefits", Published at MDIP, Published on [Sep. 25, 2019] https://www.mdpi.com/1424-8220/19/19/4157.

"A review of air filtration technologies for sustainable and healthy building ventilation", Published at Sustainable Cities and Society, Published on [Jul. 2017] https://core.ac.uk/download/pdf/84587706.pdf.

"A novel constant-air-vol. range hood for high-rise residential buildings with 2 central shaft", Published at Energy and Buildings, Published on [May 2021] http://surl.li/feadf.

"Thermodynamic performance evaluation of HFC refrigerants for the chiller system simulated by hot gas bypass cycle", Published at ZANCO Journal of Pure and Applied Sciences, Published on [Dec. 28, 2017] http://surl.li/feadr.

"An Automatic and Accurate Localization System for Firefighters", Published at Third International Conference on Internet-of-Things Design and Implementation (IoTDI), Published on [May 28, 2018] https://www.cs.virginia.edu/~stankovic/psfiles/breadcrumb_localization.pdf.

"Fire Safety", Published at Atomic Energy Regulatory Board India, Published on [May 2019] https://aerb.gov.in/images/PDF/fire.pdf.

"Fire Service Features of Buildings and Fire Protection Systems", Published at Occupational Safety and Health Administration (OSHA), Published on [Sep. 8, 2014] https://www.osha.gov/sites/default/files/publications/OSHA3256.pdf.

"A comprehensive review on indoor air quality monitoring systems for enhanced public health", Published at Sustainable Environment Research, Published on [Dec. 2020] https://sustainenvironres.biomedcentral.com/counter/pdf/10.1186/s42834-020-0047-y.pdf.

"Review of research on air-conditioning systems and indoor air quality control for human health", Published at International Journal of Refrigeration, Published on [Jan. 2009] https://sci-hub.hkvisa.net/10.1016/j.ijrefrig.2008.05.004.

"A review of the performance of different ventilation and airflow distribution systems in buildings", Published at Building and Environment, Published on [Dec. 18, 2013] https://www.academia.edu/27228820/A_review_of_the_performance_of_different_ventilation_and_airflow_distribution_systems_in_buildings.

"Real-time sensors for indoor air monitoring and challenges ahead in deploying them to urban buildings", Published at Science of The Total Environment , Published on [Apr. 2016] https://eprints.ncl.ac.uk/file_store/production/223286/749E8E7D-D1EF-4056-BCDD-F48812167CB1.pdf.

"Indoor air quality and energy management through real-time sensing in commercial buildings", Published at Energy and Buildings, Published on [Jan. 2016] https:/eprints.qut.edu.au/220977/1/93777.pdf.

"Compressors and Compressed Air Systems", Published at Continuing Education and Development, Found on [Mar. 2023] https://www.cedengineering.com/userfiles/Compressors%20and%20Compressed%20Air%20Systems%20R1.pdf.

"HVAC System", Published at Energy Conservation Building Code (ECBC) Tip Sheet, Published on [ Jun. 2009] https://www.keralaenergy.gov.in/files/HVAC_System_Tip_Sheet.pdf.

"Air distribution of oxygen supply through guardrail slot diffusers in high-altitude hypoxic areas", Published at Building and Environment, Published on [Apr. 2020] https://rb.gy/9ktde6.

"Air Quality Control in Mine Refuge Chamber with Ventilation through Pressure Air Pipeline", Published at Process Safety and Environmental Protection, Published on [Dec. 2019] https://uhra.herts.ac.uk/bitstream/handle/2299/23249/Manuscript.pdf;jsessionid=6F0E7E29FB3FF03D59759181BA6A6161?sequence=1.

"Rescue Air for Firefighters", Published at Fire Engineering, Published on [Sep. 8, 2014] https://rescueair.com/wp-content/uploads/2020/03/rescue-air-for-firefighters.whitepaperpdf.render.pdf.

"The Case for Interior High-Rise Breathing Air Systems ", Published at Fire Engineering, Published on [Apr. 2012] https://rescueair.com/wp-content/uploads/2014/05/Rush-Article.pdf.

"RF Based Advance Smart Fire Safety System for Industries and Shopping Malls", Published at International Journal of Science and Research (IJSR), Published on [Dec. 2018] https://www.ijsr.net/archive/v7/12/ART20193898.pdf.

"Design and Implementation of Car Fire Detection and Automatic Car Door Opening Using IOT", Published at International Journal of Advances in Engineering and Management (IJAEM), Published on [ Jul. 7, 2022] https://jaem.net/issue_dcp/Design%20and%20Implementation%20of%20Car%20Fire%20Detection%20and%20Automatic%20Car%20Door%20Opening%20Using%20Iot.pdf.

"Machine Vision Based Fire Detection Techniques: A Survey", Published at Springer Nature, Published on [Nov. 27, 2020] https://sci-hub.hkvisa.net/10.1007/s10694-020-01064-z.

"An Analysis of Firefighter Breathing Air Replenishment Systems", Published at Fire Protection Research Foundation, Published o[Apr. 2021] https://www.nfpa.org/-/media/Files/News-and-Research/Fire-statistics-and-reports/Emergency-responders/RFFAnalysisOfFFBARS.pdf.

"Fire Detection Systems in Wireless Sensor Networks", Published at World Conference on Technology, Innovation and Entrepreneurship, Published on [Jul. 3, 2015] https://www.sciencedirect.com/science/article/pii/S1877042815038872.

"Fire Safety System Building", Published at IOP Conference Series: Materials Science and Engineering, Published on [Nov. 2019] https://www.researchgate.net/publication/337402246_Fire_Safety_System_Building/fulltext/5dd573ae299bf11ec866bf2c/Fire-Safety-System-Building.pdf.

"SmartFire: Intelligent Platform for Monitoring Fire Extinguishers and Their Building Environment", Published at MDPI, Published on [May 25, 2019] https://www.mdpi.com/1424-8220/19/10/2390.

(56)                References Cited

OTHER PUBLICATIONS

"A Smart Fire Detection System using IoT Technology With Automatic Water Sprinkler", Published at International Journal of Electrical and Computer Engineering (IJECE), Published on [Oct. 7, 2020] http://surl.li/esuhn.

"Situational Awareness for first responders: Evaluation of the BIMS field trial", Published at IEEE Xplore, Published on [Dec. 9, 2009] http://surl.li/esuid.

"Fire Safety in Buildings", Published at Journal of Civil & Environmental Engineering, Published on [Jan. 2017] https://www.researchgate.net/profile/Noah-Akhimien/publication/328075851_Fire_Safety_in_Buildings/links/5bb62f01299bf1049b6f57d7/Fire-Safety-in-Buildings.pdf.

"Ignis: Fire Detection and Mitigation System", Published at International Research Journal of Engineering and Technology (IRJET), Published on [Jun. 6, 2021 ] https://www.irjet.net/archives/V8/i6/IRJET-V816493.pdf.

"An Intelligent Fire Detection and Mitigation System Safe from Fire (SFF)s", Published at International Journal of Computer Applications, Published on [Jan. 2016] https://www.ijcaonline.org/research/volume133/number6/mobin-2016-ijca-907858.pdf.

"Smart Fire Alert System Using IOT", Published at International Research Journal of Modernization in Engineering Technology and Science, Published on [Mar. 3, 2022 ] https://www.irjmets.com/uploadedfiles/paper/issue_3_march_2022/20213/final/fin_irjmets1648303966.pdf.

"Johnson Controls Acquires Rescue Air Systems To Enhance Fire Suppression Portfolio", Published atTheBigRedGuide, Published on [Oct. 6, 2022] https://www.thebigredguide.com/docs/opdf/news/johnson-controls-acquires-rescue-air-systems-enhance-fire-suppression-portfolio-co-5246-ga-co-1665048943-ga.1665049545.pdf.

"5.07 Air Replenishment Systems (2019)", Published at San Francisco Fire Department Bureau of Fire Prevention & Investigation, Found Online on [Feb. 8, 2014] https://sf-fire.org/media/1220/download?inline.

"Summary of Compressed Air Samples from Firefighter Air Replenishment Systems (FARS)", Published at Firefighter Air Coalition, Published on [May 15, 2020] https://aircoalition.org/wp-content/uploads/2021/03/Trace-Analytics-FARS-Air-Quality-Report.pdf.

"Firefighter Air Replenishment Systems (FARS) Air Quality Fact Sheet ", Published at Firefighter Air Coalition, Publish Online on [Feb. 8, 2014] https://aircoalition.org/wp-content/uploads/2021/03/FAC-FARS-Air-Quality-White-Paper.pdf.

"Technical Brief on System Controls for Industrial Compressed Air Systems", Published at Compressed Air And Gas Institute, Found Online on [Feb. 15, 2022] https://www.cagi.org/assets/documents/pdfs/SystemControlsTechnicalBrief.pdf?updated=1657712699.

"Case Study—System Controls", Published at Compressed Air And Gas Institute, Found Online on [Feb. 15, 2022] https://www.cagi.org/assets/documents/pdfs/SystemControlsCaseStudy.pdf?updated=1657712699.

"Technical Brief—Heat Recovery from Industrial Compressed Air Systems", Published at Compressed Air And Gas Institute, Found Online on [Feb. 15, 2022] https://www.cagi.org/assets/documents/pdfs/HeatRecoveryTechnicalBrief.pdf?updated=1657712699.

"Technical Brief on Distribution Piping Network", Published at Compressed Air And Gas Institute, Found Online on [Feb. 15, 2022] https://www.cagi.org/assets/documents/pdfs/DistributionPipingNetworkTechnicalBrief.pdf?updated=1657712699.

"Technical Brief on Pressure Drop", Published at Compressed Air And Gas Institute, Found Online on [Feb. 15, 2022] https://www.cagi.org/assets/documents/pdfs/PressureDropTechnicalBrief.pdf?updated=1657712700.

"Technical Brief on Variable Speed Drive", Published at Compressed Air And Gas Institute, Found Online on [Feb. 15, 2022] https://www.cagi.org/assets/documents/pdfs/VariableSpeed-DriveTechnicalBrief.pdf?updated=1657712699.

"Compressor Room Advantages with Oil-Free Centrifugal Air Compressors", Published at Compressed Air And Gas Institute, Found Online on [Feb. 15, 2022] https://www.cagi.org/pdf/downloads/compressor-room-advantages-with-oil-free-centrifugal-air-compressors.

"Preparing Reciprocating Air Compressors for Winter", Published at Compressed Air And Gas Institute, Found Online on [Feb. 15, 2022] https://www.cagi.org/pdf/downloads/preparing-reciprocating-air-compressors-for-winter.

"Nitrogen Characteristics and Benefits of On-Site Generation", Published at Compressed Air And Gas Institute, Found Online on [Feb. 15, 2022] https://www.cagi.org/pdf/downloads/19-nitrogen-characteristics-and-benefits-of-on-site-generation.

"Key Considerations for Installing Centrifugal Air Compressors", Published at Compressed Air And Gas Institute, Found Online on [Feb. 15, 2022] https://www.cagi.org/pdf/downloads/20-key-considerations-for-installing-centrifugal-air-compressors.

"Compressed Air & Gas Handbook", Published at Compressed Air And Gas Institute, Found Online on [Feb. 15, 2022] https://www.cagi.org/handbook-pdfs/handbook-chapter-1.

"Climate Change: Atmospheric Carbon Dioxide", Published at NOAA Climate, Publish on [Jun. 23, 2022] https://www.climate.gov/news-features/understanding-climate/climate-change-atmospheric-carbon-dioxide.

"Fire Hazard in Buildings: Review,Assessment and Strategies For Improving Fire Safety", Published at Emerald Insight, Publish on [Dec. 28, 2018] https://www.emerald.com/insight/content/doi/10.1108/PRR-12-2018-0033/full/pdf?title=fire-hazard-in-buildings-review-assessment-and-strategies-for-improving-fire-safety.

"Environmental Study Of Firefighters", Published at University of California, Publish on [Sep. 8, 2015] https://sci-hub.hkvisa.net/10.1093/annhyg/35.6.581.

"Summary of human responses to ventilation", Published at California Digital Library University of Clifiornia, Publish on [Jun. 1, 2004] https://escholarship.org/content/qt64k2p4dc/qt64k2p4dc.pdf.

"Fixed Fire Protection Systems in Tunnels:Issues and Directions", Published at Fire Technology, Publish on [Sep. 30, 2010] https://sci-hub.hkvisa.net/10.1007/s10694-011-0220-2.

"Comparison of Underfloor Vs. Overhead Air Distribution Systems in an Office Building", Published at Department of Architecture, Waseda University, Found Online on [Feb. 15, 2022] https://www.airfixture.com/wp-content/uploads/2016/07/ASHRAE-Underfloor-vs-Overhead-Study.pdf.

"General Requirements in piping Design", Published at RMIT University in partnership with Informit Open, Publish on [Jul. 2021] https://search.informit.org/doi/epdf/10.3316/informit.947188479100130.

"Optimal operation of heat supply systems with piping network", Published at Department of Mechanical Engineering, Osaka Prefecture University, Publish on [ Oct. 14, 2016] https://sci-hub.hkvisa.net/10.1016/j.energy.2017.03.146.

"Compressed Air Piping Network Inspection And Documentation For PAROC", Published at Turku University of Applied Sciences, Found Online on [Feb. 15, 2022] https://www.theseus.fi/bitstream/handle/10024/122415/Myllyniemi_Jani.pdf?sequence=1.

"Natural Gas Pipeline Technology Overview", Publish at Argonne National Laboratory, Publish on [ Nov. 2007] https://publications.anl.gov/anlpubs/2008/02/61034.pdf.

"Improving the indoor air quality using the individual air supply system", Publish at Int. J. Environ. Sci. Technol., Publish on [ Jul. 24, 2017] https:/link.springer.com/content/pdf/10.1007/s13762-017-1432-x.pdf?pdf=button.

"Analytical Modeling of Fire Smoke Spread in High-rise Buildings", Publish at Concordia University Montreal, Quebec, Canada Publish on [ Sep. 2016] https://core.ac.uk/download/pdf/211519293.pdf.

"Chapter 6 Fire-Fighting Systems" https://www.globalsecurity.org/military/library/policy/navy/nrtc/14057_ppr_ch6.pdf.

"Research and Perspectives on Fire-Fighting Systems in Tunnels under Strong Piston Wind Action", By Xiaoyi Zhao et al., Published at Construction Management, and Computers & Digitization, Published on [Jan. 31, 2023] https://www.mdpi.com/2075-5309/13/2/435.

"Wireless sensor network applications in monitoring and control of gas networks ", By Sajad Balall Dehkordi et al., Published at

(56) References Cited

OTHER PUBLICATIONS

Majlesi Journal of Telecommunication Devices , Published on [Jun. 23, 2012] https://mjtd.isfahan.lau.ir/article_695667_a4c0e30293098b0ac5497f27c43f5bb9.pdf.

"Sustainability of Air Supply in Areas Immediately Dangerous to Life and Health", By Christopher W. Norris, Published at Northampton Fire Department,MA , Published in [Feb. 2008] https://apps.usfa.fema.gov/pdf/efop/efo41710.pdf.

"Sensor-based safety management", By Amin Asadzadeh et al., Published at Automation in Construction , Published on [Feb. 7, 2020] https://sci-hub.hkvisa.net/10.1016/j.autcon.2020.103128.

"Remote Monitoring and Control Using Mobile Phones", By Dr. Mikael Sjodin, Published at Newline Information , Published in [Nov. 2001] http://www.es.mdh.se/pdf_publications/413.pdf.

"Monitored Performance of an Office Buildingwith an Under-Floor Air Distribution System", By Christine E. Walker et al., Published at Fifth International Conference for Enhanced Building Operations, Pittsburgh, Pennsylvania , Published on [Oct. 13, 2005] https://oaktrust.library.tamu.edu/bitstream/handle/1969.1/5105/ESL-IC-5-10-13.pdf?sequence=4.

"Investigating Accessibility of Social Security System (SSS) Mobile Application: A Structural Equation Modeling Approach", Yung-Tsan Jou, Published at Sustainability 2022, Published on [Jun. 29, 2022] https://www.mdpi.com/2071-1050/14/13/7939.

"Firefighter Fatalities in the US in 2021", By Richard Campbell et al., Published at National Fire Protection Association (NFPA), Published in [Jun. 2023] https://www.nfpa.org/-/media/Files/News-and-Research/Fire-statistics-and-reports/Emergency-responders/osFFF.pdf.

"Reversible Longitudinal Smoke Extraction System in Enclosed Underground Parking Structure", By KongKok Haw, Published at Journal of Advanced Research in Fluid Mechanics and Thermal Sciences, Published on [Mar. 2, 2019] https://www.akademiabaru.com/submit/index.php/arfmts/article/view/2470/1450.

"Mapping Fire and Firefighter Visibility for Improving Situational Awareness", By Katherine Ann Mistick, Published at The University of Utah ProQuest Dissertations , Published in [May 2022] https://www.proquest.com/openview/089c0ac0998979da3b550b77ddee2bf1/1?pq-origsite=gscholar&cbl=18750&diss=y.

"An ultra-wide band indoor personnel tracking system for emergency situations (Europcom)", By Anthony Putorti Jr. et al., Published at Radar Conference, 2008. EuRAD 2008. European, Published in [Dec. 2008] http://surl.ll/hqxep.

"Threat modeling in smart firefighting systems: Aligning MITRE ATT&CK matrix and NIST security controls", Shahzaib Zahid et al., Published at Internet of Things, Published on [Mar. 21, 2023] https://tinyurl.com/msjusd3y.

"Autonomous Fire Suppression Systemfor Use in High and Low VisibilityEnvironments by Visual Servoing", By Joshua G. McNeil et al., Published at Fire Technology 2016, Published on [ Jan. 7, 2016] https://sci-hub.hkvisa.net/10.1007/s10694-016-0564-8.

"Breathing Limited Air Situational Training Masks (BlastMask) Versus SelfContained Breathing Apparatus (SCBA) for Firefighters: A Pilot Study", By Thomas L. Andre et al., Published at International journal of exercise science, Published in [2019] https://digitalcommons.wku.edu/cgi/viewcontent.cgi?article=2498&context=ijes.

"Internet of Things technology for fire monitoring system", By S.R. Vijayalakshmi et al., Published at International Research Journal of Engineering and Technology (IRJET), Published on [Jun. 6, 2017] https://www.irjet.net/archives/V4/16/IRJET-V4I6418.pdf.

"Firefighter Safety Using IoT", By Caroline Jebakumari S et al., Published at Recent Trends in Intensive Computing, Published in [Dec. 2021] https://www.researchgate.net/publication/356753949_Firefighter_Safety_Using_IoT/fulltext/61aa2f9e50e22929cd4342f7/Firefighter-Safety-Using-IoT.pdf.

"A smart fire detection system using IoT technology with automatic water sprinkler", By Hamood Alqourabah et al., Published at International Journal of Electrical and Computer Engineering (IJECE), Published on [ Mar. 5, 2021] https://pdfs.semanticscholar.org/f3e7/a7c0cf2d448be592421045033506e845e6c2.pdf.

"Route Planning for Fire Rescue Operations in Long-Term Care Facilities Using Ontology and Building Information Models", By Ru-Guan Wang et al., Published at Building Information Modelling, Semantic Web and Internet-of-Things for Smart Cities, Published on [Jul. 21, 2022] https://www.mdpi.com/2075-5309/12/7/1060?type=check_update&version=2.

International Search Report and Written Opinion for Appl. Ser. No. PCT/IB2024/050603 dated Apr. 24, 2024 (10 pages).

International Search Report and Written Opinion issued in connection with PCT/US2023/014763 dated Jun. 21, 2023 (8 pages).

International Search Report and Written Opinion issued in connection with PCT/US2023/014764 dated Jun. 23, 2023 (9 pages).

International Search Report and Written Opinion issued in connection with PCT/US2023/014765 dated Jun. 27, 2023 (10 pages).

International Search Report and Written Opinion issued in connection with PCT/US2023/017653 dated Jul. 24, 2023 (9 pages).

International Search Report and Written Opinion issued in connection with PCT/US2023/017656 dated Jul. 19, 2023 (10 pages).

International Search Report and Written Opinion issued in connection with PCT/US2023/017803 dated Jul. 24, 2023 (8 pages).

International Search Report and Written Opinion issued in connection with PCT/US2023/018401 dated Jul. 27, 2023 (10 pages).

International Search Report and Written Opinion issued in connection with PCT/US2023/019880 dated Aug. 2, 2023 (8 pages).

International Search Report and Written Opinion issued in connection with PCT/US2023/022222 dated Aug. 24, 2023 (11 pages).

International Search Report and Written Opinion issued in connection with PCT/US2023/022223 dated Sep. 4, 2023 (7 pages).

International Search Report and Written Opinion issued in connection with PCT/US2023/024766 dated Oct. 4, 2023 (7 pages).

International Search Report and Written Opinion issued in connection with PCT/US2023/025646 dated Oct. 11, 2023 (10 pages).

International Search Report and Written Opinion issued in connection with PCT/US2023/025647 dated Oct. 4, 2023 (10 pages).

International Search Report and Written Opinion issued in connection with PCT/US2023/026172 dated Oct. 31, 2023 (9 pages).

International Search Report and Written Opinion issued in connection with PCT/US2023/026174 dated Oct. 20, 2023 (7 pages).

International Search Report and Written Opinion issued in connection with PCT/US2023/026176 dated Oct. 17, 2023 (7 pages).

International Search Report and Written Opinion issued in connection with PCT/US2023/026425 dated Oct. 17, 2023 (12 pages).

International Search Report and Written Opinion issued in connection with PCT/US2023/026428 dated Oct. 17, 2023 (8 pages).

International Search Report and Written Opinion issued in connection with PCT/US2023/026466 dated Nov. 1, 2023 (8 pages).

Bhatnagar et al., "Machine Learning Techniques to Reduce Error in the Internet of Things," IEEE, 9th International Conference on Cloud Computing, Data Science & Engineering—Confluence—(pp. 403-408).

Enmet—Product Information, "Compressed Airline Monitors & Respiratory Air Monitors & Portable Breathing Air Systems," 2025 (2 pages).

Kinaeva et al., "Machine Learning Algorithms for Regression Analysis and Predictions of Numerical Data," 2021 3rd International Congress on Human-Computer Interaction, Optimization and Robotic Applications, 2021 (pp. 1-6).

Rush III, J.D., "Monitor Your Air Supply" Fire Engineering, 2014 (2 pages).

Trevino, "What Every Firefighter Needs to Know About FARS," Fire Apparatus & Emergency Equipment, 2016 (pp. 1-8).

* cited by examiner

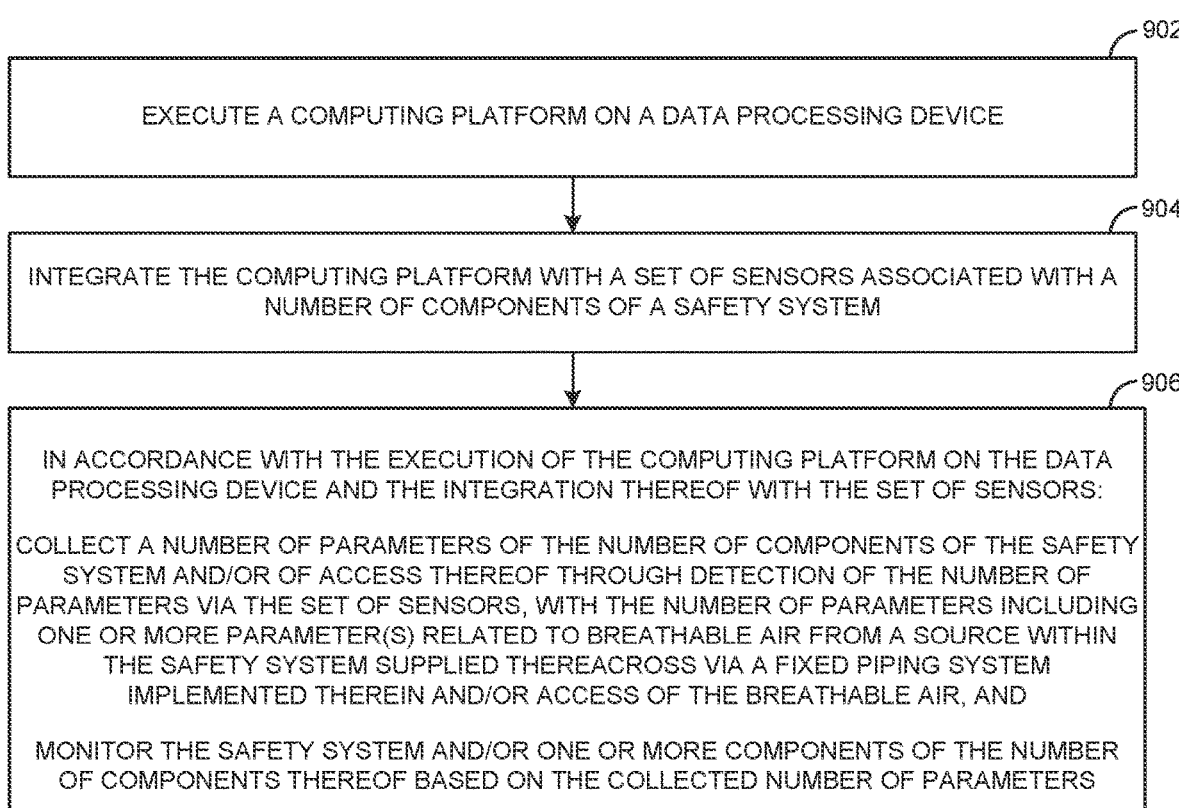

902

EXECUTE A COMPUTING PLATFORM ON A DATA PROCESSING DEVICE

904

INTEGRATE THE COMPUTING PLATFORM WITH A SET OF SENSORS ASSOCIATED WITH A NUMBER OF COMPONENTS OF A SAFETY SYSTEM

906

IN ACCORDANCE WITH THE EXECUTION OF THE COMPUTING PLATFORM ON THE DATA PROCESSING DEVICE AND THE INTEGRATION THEREOF WITH THE SET OF SENSORS:

COLLECT A NUMBER OF PARAMETERS OF THE NUMBER OF COMPONENTS OF THE SAFETY SYSTEM AND/OR OF ACCESS THEREOF THROUGH DETECTION OF THE NUMBER OF PARAMETERS VIA THE SET OF SENSORS, WITH THE NUMBER OF PARAMETERS INCLUDING ONE OR MORE PARAMETER(S) RELATED TO BREATHABLE AIR FROM A SOURCE WITHIN THE SAFETY SYSTEM SUPPLIED THEREACROSS VIA A FIXED PIPING SYSTEM IMPLEMENTED THEREIN AND/OR ACCESS OF THE BREATHABLE AIR, AND

MONITOR THE SAFETY SYSTEM AND/OR ONE OR MORE COMPONENTS OF THE NUMBER OF COMPONENTS THEREOF BASED ON THE COLLECTED NUMBER OF PARAMETERS

FIG. 9

METHOD, DEVICE AND SYSTEM OF A SENSOR INTEGRATED COMPUTING PLATFORM OF A FIREFIGHTER AIR REPLENISHMENT SYSTEM FOR REMOTE MONITORING AND ACCESS THEREOF

CLAIM OF PRIORITY

This application is a conversion application of, and claims priority to, U.S. Provisional Patent Application No. 63/356,996 titled CLOUD-BASED FIREFIGHTING AIR REPLENISHMENT MONITORING SYSTEM, SENSORS AND METHODS filed on Jun. 29, 2022 and U.S. Provisional Patent Application No. 63/359,882 titled REMOTE MONITORING AND CONTROL OF A FIREFIGHTER AIR REPLENISHMENT SYSTEM THROUGH SENSORS DISTRIBUTED WITHIN COMPONENTS OF THE FIREFIGHTER AIR REPLENISHMENT SYSTEM filed on Jul. 11, 2022. The contents of each of the aforementioned applications are incorporated herein by reference in entirety thereof.

FIELD OF TECHNOLOGY

This disclosure relates generally to emergency systems and, more particularly, to a method, a device and/or a system of a sensor integrated computing platform of a safety system of a structure for remote monitoring and access thereof.

BACKGROUND

A structure (e.g., a vertical building, a horizontal building, a tunnel, marine craft) may have a Firefighter Air Replenishment System (FARS) implemented therein. The FARS may have an emergency air fill station therein to enable firefighters and/or emergency personnel access breathable air therethrough. The FARS may have other components relevant to critical functioning thereof. However, tracking parameters (e.g., pressure of the breathable air supplied) of the FARS critical to the functioning and/or the maintenance thereof may be difficult due to a monolithic and/or a standalone implementation of the components of the FARS.

SUMMARY

Disclosed are a method, a device and/or a system of a sensor integrated computing platform of a safety system of a structure for remote monitoring and access thereof.

In one aspect, a method of a safety system of a structure having a fixed piping system implemented therein to supply breathable air from a source across the safety system is disclosed. The method includes executing a computing platform on a data processing device, and integrating the computing platform with a set of sensors associated with a number of components of the safety system. In accordance with the execution of the computing platform on the data processing device and the integration thereof with the set of sensors, the method also includes, through the data processing device, collecting a number of parameters of the number of components of the safety system and/or of access thereof through detection of the number of parameters via the set of sensors. The number of parameters includes one or more parameter(s) related to the breathable air and/or access of the breathable air. Further, the method includes monitoring the safety system and/or one or more component(s) of the number of components thereof based on the collected number of parameters.

In another aspect, a data processing device of a safety system of a structure having a fixed piping system implemented therein to supply breathable air from a source across the safety system is disclosed. The data processing device includes a memory including instructions associated with a computing platform stored therein, and a processor communicatively coupled to the memory. The processor executes the instructions associated with the computing platform to integrate the computing platform with a set of sensors associated with a number of components of the safety system, and, in accordance with the integration, collect a number of parameters of the number of components of the safety system and/or of access thereof through detection of the number of parameters via the set of sensors. The number of parameters includes one or more parameter(s) related to the breathable air and/or access of the breathable air. The processor also executes the instructions associated with the computing platform to monitor the safety system and/or one or more component(s) of the number of components thereof based on the collected number of parameters.

In yet another aspect, a safety system of a structure having a fixed piping system implemented therein to supply breathable air from a source across the safety system is disclosed. The safety system includes a data processing device executing a computing platform thereon, and a set of sensors associated with a number of components of the safety system. The execution of the computing platform on the data processing device integrates the computing platform with the set of sensors associated with the number of components of the safety system. In accordance with the execution of the computing platform on the data processing device and the integration thereof with the set of sensors, the data processing device collects a number of parameters of the number of components of the safety system and/or of access thereof through detection of the number of parameters via the set of sensors. The number of parameters includes one or more parameter(s) related to the breathable air and/or access of the breathable air. The data processing device also monitors the safety system and/or one or more component(s) of the number of components thereof based on the collected number of parameters.

Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which:

FIG. 9 is a process flow diagram detailing the operations involved in realizing a sensor integrated computing platform of a safety system of a structure for remote monitoring and access thereof, according to one or more embodiments.

Other features of the present embodiments will be apparent from the accompanying drawings and from the detailed description that follows.

DETAILED DESCRIPTION

Example embodiments, as described below, may be used to provide a method, a device and/or a system of a sensor integrated computing platform of a safety system of a structure for remote monitoring and access thereof. Although the present embodiments have been described with reference to specific example embodiments, it will be evident that various modifications and changes may be made to these embodiments without departing from the broader spirit and scope of the various embodiments.

Figure 1:
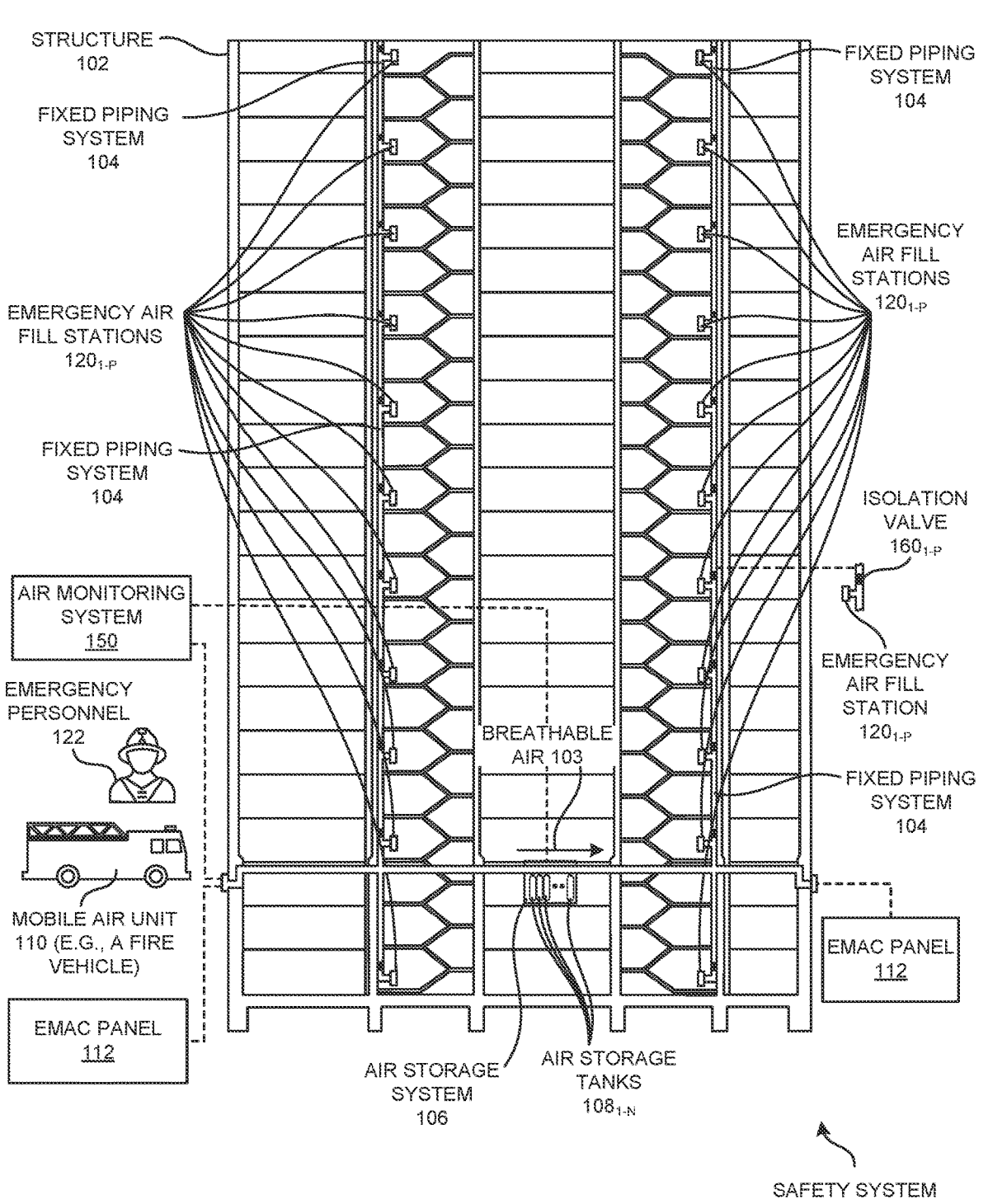
FIG. 1 is a schematic and an illustrative view of a safety system associated with a structure, according to one or more embodiments.

FIG. 1 shows a safety system 100 associated with a structure 102, according to one or more embodiments. In one or more embodiments, safety system 100 may be a Firefighter Air Replenishment System (FARS) to enable firefighters entering structure 102 in times of fire-related emergencies to gain access to breathable (e.g., human breathable) air (e.g., breathable air 103) in-house without the need of bringing in air bottles/cylinders to be transported up several flights of stairs of structure 102 or deep thereinto, or to refill depleted air bottles/cylinders that are brought into structure 102. In one or more embodiments, safety system 100 may supply breathable air provided from a supply of air tanks (to be discussed) stored in structure 102. When a fire department vehicle arrives at structure 102 during an emergency, breathable air supply typically may be provided through a source of air connected to said vehicle. In one or more embodiments, safety system 100 may enable firefighters to refill air bottles/cylinders thereof at emergency air fill stations (to be discussed) located throughout structure 102. Specifically, in some embodiments, firefighters may be able to fill air bottles/cylinders thereof at emergency air fill stations within structure 102 under full respiration in less than one to two minutes.

In one or more embodiments, structure 102 may encompass vertical building structures, horizontal building structures (e.g., shopping malls, hypermarts, extended shopping, storage and/or warehousing related structures), tunnels, marine craft (e.g., large marine vessels such as cruise ships, cargo ships, submarines and large naval craft, which may be "floating" versions of buildings and horizontal structures) and mines. Other structures are within the scope of the exemplary embodiments discussed herein. In one or more embodiments, safety system 100 may include a fixed piping system 104 permanently installed within structure 102 serving as a constant source of replenishment of breathable air 103. Fixed piping system 104 may be regarded as being analogous to a water piping system within structure 102 or another structure analogous thereto for the sake of imaginative convenience.

As shown in FIG. 1, fixed piping system 104 may distribute breathable air 103 across floors/levels of structure 102. For the aforementioned purpose, fixed piping system 104 may distribute breathable air 103 from an air storage system 106 (e.g., within structure 102) including a number of air storage tanks $108_{1-N}$ that serve as sources of pressurized/compressed air (e.g., breathable air 103). Additionally, in one or more embodiments, fixed piping system 104 may interconnect with a mobile air unit 110 (e.g., a fire vehicle) through an External Mobile Air Connection (EMAC) panel 112.

In one or more embodiments, EMAC panel 112 may be a boxed structure (e.g., exterior to structure 102) to enable the interconnection between mobile air unit 110 and safety system 100. For example, mobile air unit 110 may include an on-board air compressor to store and replenish pressurized/compressed air (e.g., breathable air analogous to breathable air 103) in air bottles/cylinders (e.g., utilizable with Self-Contained Breathing Apparatuses (SCBAs) carried by firefighters). Mobile air unit 110 may also include other pieces of air supply/distribution equipment (e.g., piping and/or air cylinders/bottles) that may be able to leverage the sources of breathable air 103 within safety system 100 through EMAC panel 112. Firefighters, for example, may be able to fill breathable air (e.g., breathable air 103, breathable air analogous to breathable air 103) into air bottles/cylinders (e.g., spare bottles, bottles requiring replenishment of breathable air) carried on mobile air unit 110 through safety system 100.

In FIG. 1, EMAC panel 112 is shown at two locations merely for the sake of illustrative convenience. In one or more embodiments, an air monitoring system 150 may be installed as part of safety system 100 to automatically track and monitor a parameter (e.g., pressure) and/or a quality (e.g., indicated by moisture levels, carbon monoxide levels) of breathable air 103 within safety system 100. FIG. 1 shows air monitoring system 150 as communicatively coupled to air storage system 106 and EMAC panel 112 merely for the sake of example. It should be noted that EMAC panel 112 may be at a remote location associated with (e.g., internal to, external to) structure 102. In one or more embodiments, for monitoring the parameters and/or the quality of breathable air within safety system 100, air monitoring system 150 include appropriate sensors and circuitries therein. For example, a pressure sensor (to be discussed) within air monitoring system 150 may automatically sense and record a pressure of breathable air 103 of safety system 100. Said pressure sensor may communicate with an alarm system that is triggered when the sensed pressure is outside a safety range. Also, in one or more embodiments, air monitoring system 150 may automatically trigger a shutdown of breathable air distribution through safety system 100 in case of impurity/contaminant (e.g., carbon monoxide) detection therethrough yielding levels above a safety/predetermined threshold.

In one or more embodiments, fixed piping system 104 may include pipes (e.g., constituted out of stainless steel tubing) that distribute breathable air 103 to a number of emergency air fill stations $120_{1-P}$ within structure 102. In one example implementation, each emergency air fill station $120_{1-P}$ may be located at a specific level of structure 102. If structure 102 is regarded as a vertical building structure, an emergency air fill station $120_{1-P}$ may be located at each of a basement level, a first floor level, a second floor level and so on. For example, emergency air fill station $120_{1-P}$ may be located at the end of the flight of stairs that emergency fighting personnel (e.g., firefighting personnel) need to climb to reach a specific floor level within the vertical building structure.

In one or more embodiments, an emergency air fill station $120_{1-P}$ may be a static location within a level of structure 102 that provides emergency personnel 122 (e.g., firefighters, emergency responders) with the ability to rapidly fill air bottles/cylinders (e.g., SCBA cylinders) with breathable air 103. In one or more embodiments, emergency air fill station $120_{1-P}$ may be an emergency air fill panel or a rupture containment air fill station. In one or more embodiments, proximate each emergency air fill station $120_{1-P}$, safety system 100 may include an isolation valve $160_{1-P}$ to isolate a corresponding emergency air fill station $120_{1-P}$ from a rest of safety system 100. For example, said isolation may be achieved through the manual turning of isolation valve $160_{1-P}$ proximate the corresponding emergency air fill station $120_{1-P}$ or remotely (e.g., based on automatic turning) from air monitoring system 150. In one example implementation, air monitoring system 150 may maintain breathable air supply to a subset of emergency air fill stations $120_{1-P}$ via fixed piping system 104 through control of a corresponding subset of isolation valves $160_{1-P}$ and may isolate the other emergency air fill stations $120_{1-P}$ from the breathable air supply. It should be noted that configurations and components of safety system 100 may vary from the example safety system 100 of FIG. 1.

Figure 2:
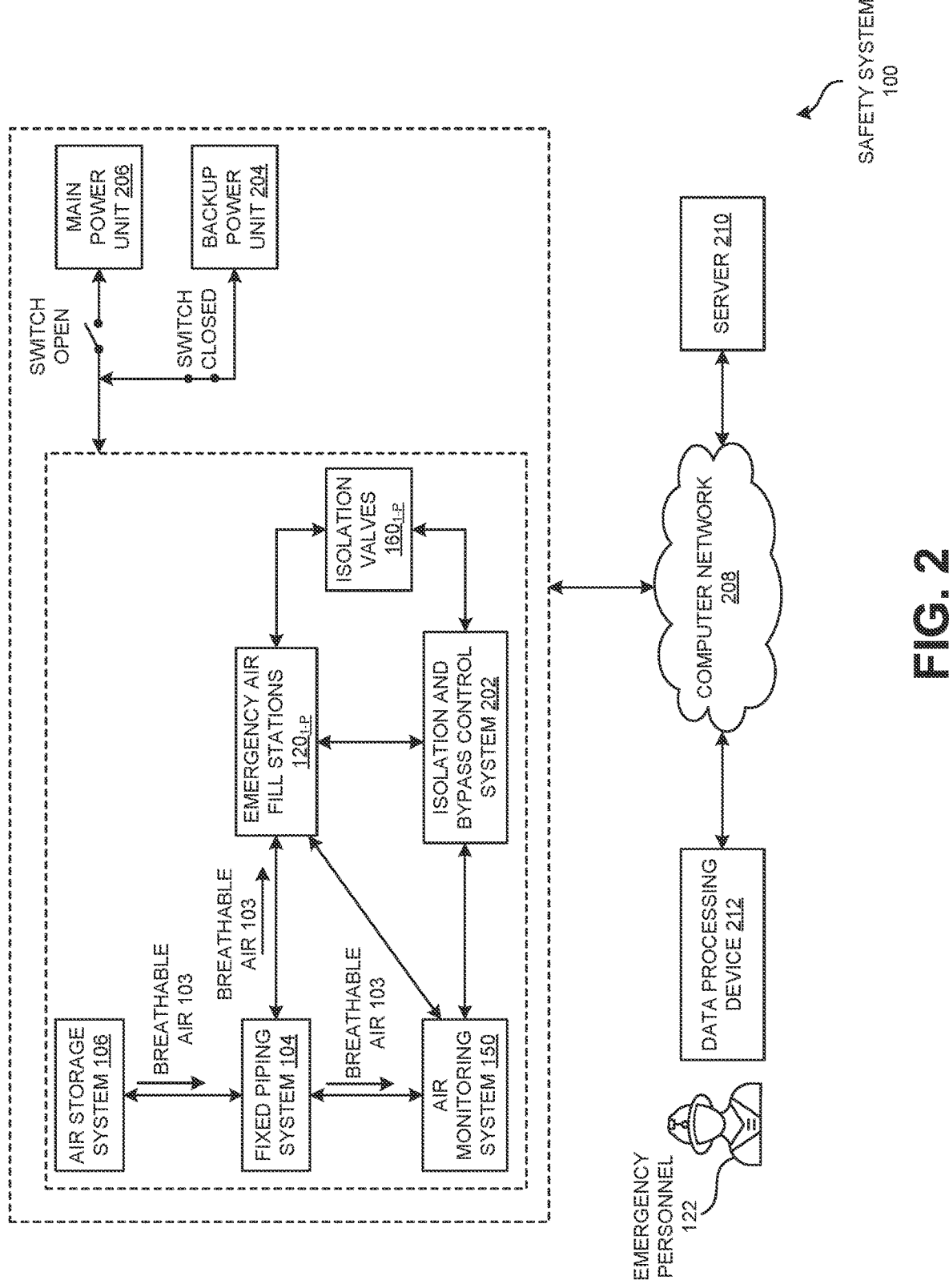
FIG. 2 is a schematic view of the safety system of FIG. 1 with elements thereof integrated therewithin in detail, according to one or more embodiments.

FIG. 2 shows safety system 100 with elements thereof integrated therewithin in detail, according to one or more embodiments. In one or more embodiments, safety system 100 may include air monitoring system 150 discussed above communicatively coupled to fixed piping system 104, to which emergency air fill stations $120_{1-P}$ are also coupled. In one or more embodiments, as seen above, the source of breathable air 103 may be air storage system 106. In one or more embodiments, safety system 100 may also include an isolation and bypass control system 202 that is constituted by a set of electrical, mechanical and/or electronic components working together to automatically include and/or bypass one or more emergency air fill station(s) $120_{1-P}$ based on detection of anomalous air parameters, as will be discussed below. For the aforementioned purpose, in one or more embodiments, isolation valve(s) $160_{1-P}$ associated with the aforementioned emergency air fill stations $120_{1-P}$ may be controlled (e.g., by opening or closing one or more of said isolation valves $160_{1-P}$) by isolation and bypass control system 202. In other words, in one or more embodiments, the one or more isolation valves $160_{1-P}$ may be opened or closed to control the flow of breathable air 103 from the source thereof to a corresponding one or more emergency air fill stations $120_{1-P}$ in response to detection of anomalous air parameters or collection of the air parameters (e.g., parameters 304, parameters 404, parameters 508 to be discussed below).

Further, in one or more embodiments, safety system 100 may include a backup power unit 204 (e.g., an electrical power system with electronic integration) to ensure uninterrupted power to components of safety system 100 during emergencies (e.g., a power cut, a mains power issue, a fire accident effected power issue). For the aforementioned purpose, in one or more embodiments, backup power unit 204 may be switched on in the case of a power related emergency with respect to a main power unit 206 (e.g., Alternating Current (AC) mains power, Direct Current (DC) power) associated with safety system 100.

In one or more embodiments, one or more or all of the abovementioned components of safety system 100 may be integrated with sensor(s) to detect parameters of use therewithin. In one or more embodiments, one or more of the aforementioned components may be communicatively coupled through a computer network 208 (e.g., a Local Area Network (LAN), a Wide Area Network (WAN), a cloud computing network, the Internet, a short-range communication network based on Bluetooth®, WiFi® and the like) to a remote server 210 (e.g., a network of servers, a single server, a distributed network of servers, a command room server associated with safety system 100 and so on). As will be discussed below, in one or more embodiments, server 210 may obtain said parameters of use and other data from safety system 100 and perform analysis (e.g., predictive, non-predictive) thereof.

In addition, in one or more embodiments, safety system 100 may include a data processing device 212 (e.g., a mobile phone, a tablet, an iPad®, a laptop, a desktop) also communicatively coupled to one or more components or each component of safety system 100 and server 210 through computer network 208. Thus, in one or more embodiments, one or more components or each component of safety system 100 may have interfaces (not explicitly shown) for wireless communication through computer network 208. Also, as will be discussed below, in one or more embodiments, wherever possible, elements (e.g., handheld Thermal Imaging Cameras (TICs), portable TICs, aerial TICs, video cameras, output audio devices, output light devices, one or more or all sensors discussed herein) may be Internet of Things (IoT) devices capable of collecting and feeding data to server 210 through computer network 208. In one or more embodiments, IoT devices (or IoT enabled devices) may be devices and/or components with programmable hardware that can transmit data over computer networks (e.g., computer network 208 such as the Internet and/or other networks); said IoT devices may include or be associated with edge devices (not shown) to control data flow at the boundaries to computer network 208.

Figure 3:
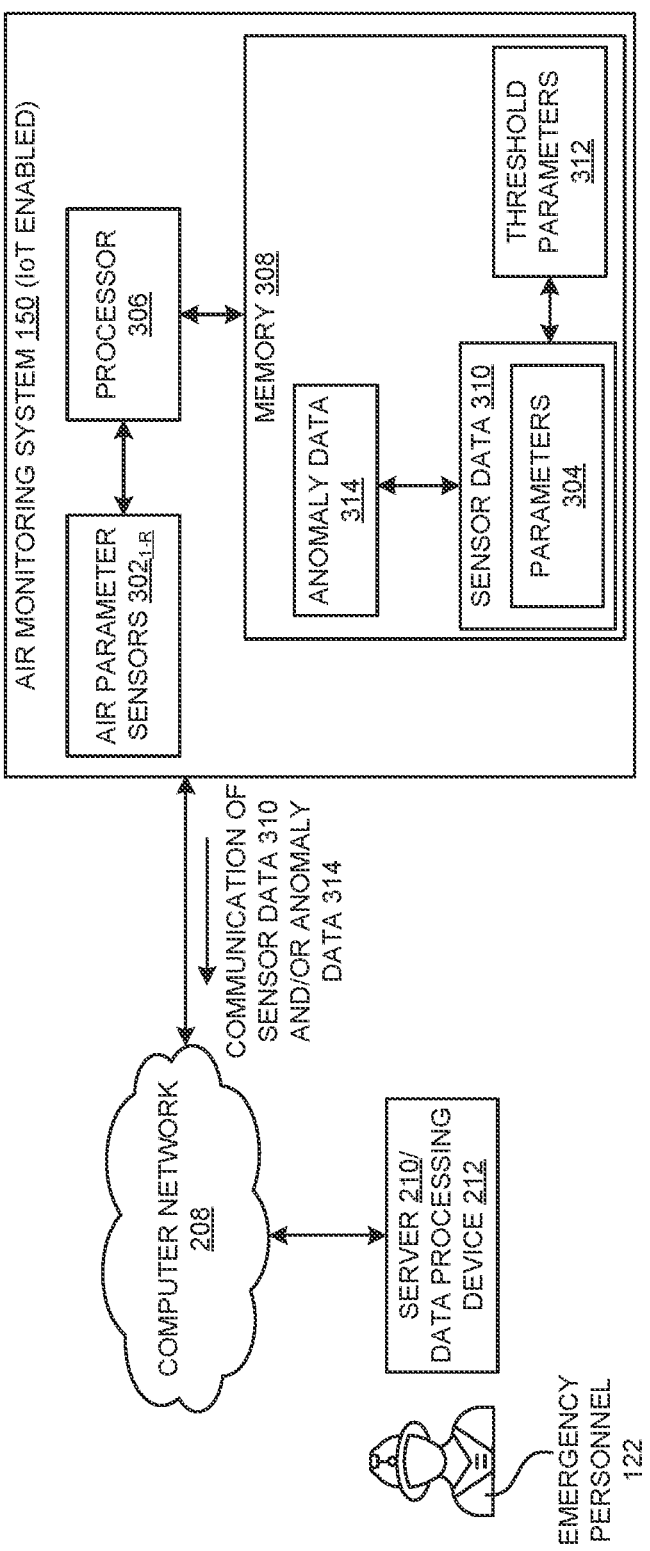
FIG. 3 is a schematic view of the air monitoring system of the safety system of FIGS. 1-2, according to one or more embodiments.

FIG. 3 shows air monitoring system 150, according to one or more embodiments. In one or more embodiments, air monitoring system 150 may include one or more air parameter sensors $302_{1-R}$ configured to sense parameters 304 associated with breathable air 103 such as pressure, temperature, oxygen content, carbon monoxide content, hydrocarbon content and moisture content; other parameters (e.g., air quality parameter(s), non-air quality parameter(s)) are within the scope of the exemplary embodiments discussed herein. In one or more embodiments, air monitoring system 150 may include a processor 306 (e.g., a microcontroller, a processor core, a single processor) communicatively coupled to a memory 308 (e.g., a volatile and/or a non-volatile memory); FIG. 3 shows air parameter sensors $302_{1-R}$ interfaced with processor 306. In one or more embodiments, data sensed by the aforementioned air parameter sensors $302_{1-R}$ may be part of sensor data 310 stored in memory 308; parameters 304 sensed may be part of sensor data 310.

Figure 4:
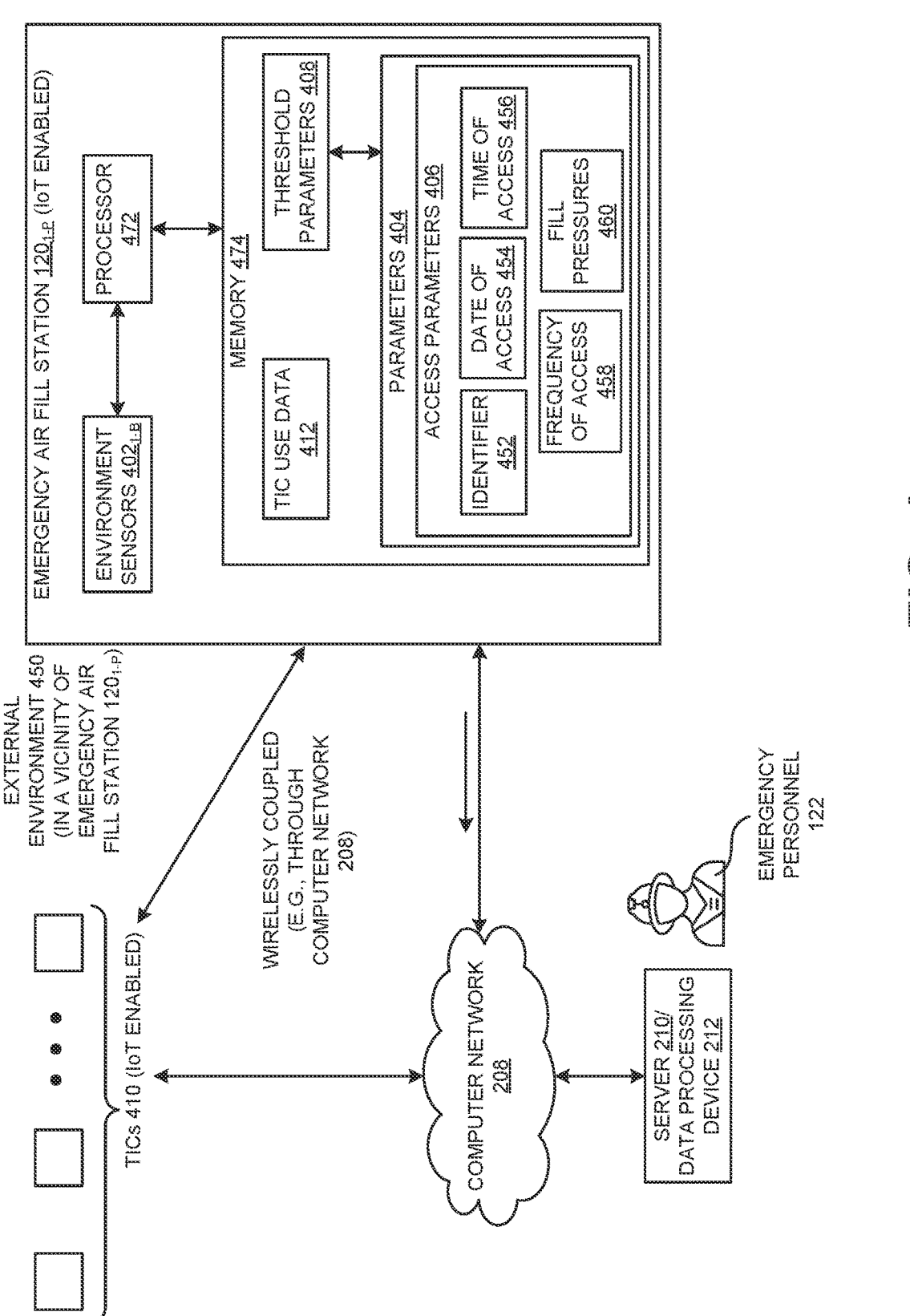
FIG. 4 is a schematic view of an emergency air fill station of the safety system of FIGS. 1-2, according to one or more embodiments.

In one or more embodiments, threshold values/ranges (e.g., threshold parameters 312) for parameters 304 sensed may also be stored in memory 308. In one or more embodiments, detecting through processor 306 in conjunction with one or more air parameter sensors $302_{1-R}$ that one or more parameters 304 is outside (e.g., below, above, outside) threshold parameters 312 may cause communication of anomalies (e.g., detected anomaly data 314 stored in memory 308) to server 210 through computer network 208 in accordance with the IoT capabilities discussed above. FIG. 4 shows an emergency air fill station $120_{1-P}$, according to one or more embodiments. Again, in one or more embodiments, emergency air fill station $120_{1-P}$ may include one or more environment sensors $402_{1-B}$ integrated therewith configured to sense parameters 404 (e.g., temperature, ambient light) of an environment (e.g., external environment 450) in an immediate vicinity of emergency air fill station $120_{1-P}$. In one or more embodiments, environment sensors $402_{1-B}$ may also sense access (e.g., access parameters 406 that are part of parameters 404 in FIG. 4) of emergency air fill station $120_{1-P}$ by emergency personnel 122 (e.g., maintenance personnel, firefighters, emergency responders). Example access parameters 406 may include but are not limited to identifier 452 of emergency personnel 122, date of access 454 mapped to identifier 452, time of access 456 mapped to identifier 452, a frequency of access 458 and fill pressures 460 (e.g., pressures to which breathable air 103 is filled in air bottles/cylinders discussed above) mapped to identifier 452, time of access 456 and/or date of access 454.

In one or more embodiments, again based on sensed parameters 404 being outside (e.g., more than, less than, outside a range) threshold values/ranges (e.g., threshold parameters 408) based on the IoT capabilities discussed herein, anomalies in parameters 404 may be detected and collected at emergency air fill station $120_{1-P}$ and transmitted to server 210 through computer network 208. In one or more embodiments, as shown in FIG. 4, emergency air fill station $120_{1-P}$ may include a processor 472 (e.g., a microcontroller, a processor core, a single processor) communicatively coupled to a memory 474 (e.g., a volatile and/or a non-volatile memory). In one or more embodiments, environment sensors $402_{1-B}$ may be interfaced with processor 472 and all of the abovementioned data/parameters may be stored in memory 474, as shown in FIG. 4.

FIG. 4 also shows TICs 410 as part of safety system 100 and in external environment 450 of emergency air fill station $120_{1-P}$, according to one or more embodiments. In one or more embodiments, TICs 410 may be infrared cameras that sense infrared energy of objects to render images/video frames thereof corresponding to surface temperatures of said objects. In one or more embodiments, emergency personnel 122 may employ said TICs 410 to detect obstacles on the paths to/around emergency air fill stations $120_{1-P}$ under low visibility; this may enable emergency personnel 122 perform rescue operations efficiently. As discussed and implied above, TICs 410 may be integrated with IoT capabilities to transmit data to server 210 through computer network 208. Said data may be part of access parameters 406 or separate data (e.g., TIC use data 412) transmitted to server 210.

It should be noted that the sensing, detection and/or transmission of data to server 210 discussed above with regard to emergency air fill station $120_{1-P}$ may also be performed at a device external to emergency air fill station $120_{1-P}$. In such implementations, the external device itself may obviously be a component of safety system 100 with IoT/wireless communication capabilities. All reasonable variations are within the scope of the exemplary embodiments discussed herein.

Figure 5:
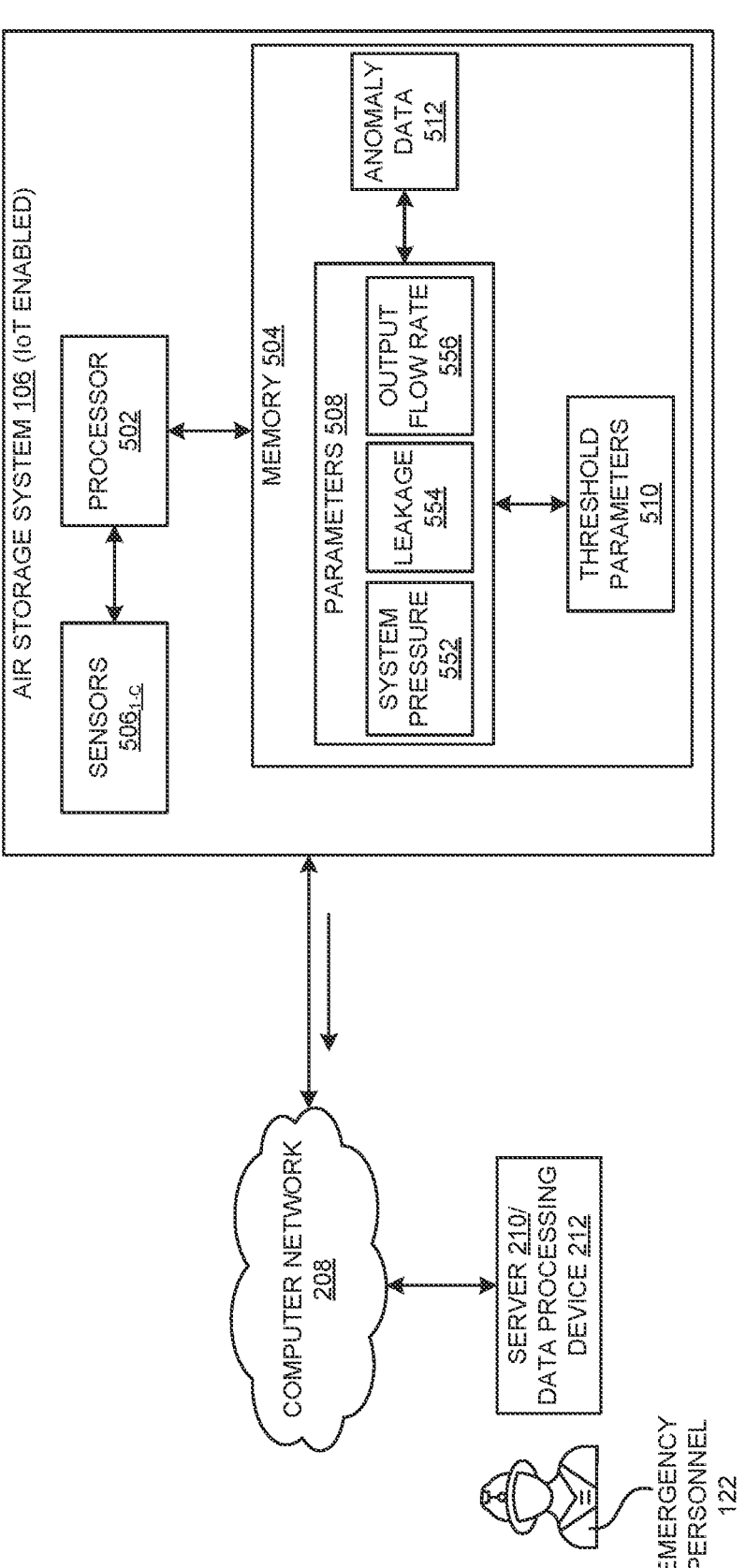
FIG. 5 is a schematic view of an air storage system of the safety system of FIGS. 1-2, according to one or more embodiments.

FIG. 5 shows air storage system 106, according to one or more embodiments. Again, as discussed above, in one or more embodiments, air storage system 106 may have IoT/wireless communication capabilities embedded therein or in a device external thereto that is communicatively coupled to air storage system 106. In one or more embodiments, air storage system 106 may include a processor 502 (e.g., a microcontroller, a processor core, a single processor) communicatively coupled to a memory 504 (e.g., a volatile and/or a non-volatile memory). Again, in one or more embodiments, air storage system 106 may include one or more sensors $506_{1-C}$ configured to sense parameters (e.g., parameters 508 stored in memory 504) associated with air storage system 106; sensors $506_{1-C}$ are shown interfaced with processor 502 Example parameters 508 sensed may include but are not limited to system pressure 552 (e.g., pressure at which breathable air 103 is output from air storage system 106), leakage 554 (e.g., leakage of breathable air 103 from air storage tanks $108_{1-N}$) and output flow rate 556 (e.g., rate of flow of breathable air 103 out of air storage system 106). In one or more embodiments, parameters 508 may be transmitted to server 210 through computer network 208 for processing and/or analysis thereat.

Again, in one or more embodiments, anomalies based on parameters 508 being outside thresholds/ranges (e.g., threshold parameters 510 stored in memory 504) may be detected through sensors $506_{1-C}$ (e.g., flow rate sensors, pressure sensors). FIG. 5 shows anomaly data 512 relevant to the aforementioned detected anomalies also transmitted to server 210 through computer network 208, according to one or more embodiments.

It should be noted that FIGS. 3-5 merely relate to example components of safety system 100 with which sensors/IoT devices are integrated and that integration of sensors/IoT devices with any other component (e.g., backup power unit 204 to sense frequency and/or duration of use thereof, isolation and bypass control system 202 to sense a frequency of bypass/isolation of emergency air fill stations $120_{1-P}$, turning on/off of isolation valves $160_{1-P}$ and so on) thereof conceivable is within the scope of the exemplary embodiments discussed herein. Referring back to FIG. 4, identifier 452 within access parameters 406 relevant to access of emergency air fill station $120_{1-P}$ may also encompass a key fob based identification, a Radio Frequency Identification (RFID) based access, a Non-Fungible Token (NFT) based access, keys and/or access through an application component (e.g., component 706 to be discussed below) executing on data processing device 212. All reasonable variations are within the scope of the exemplary embodiments discussed herein.

Figure 6:
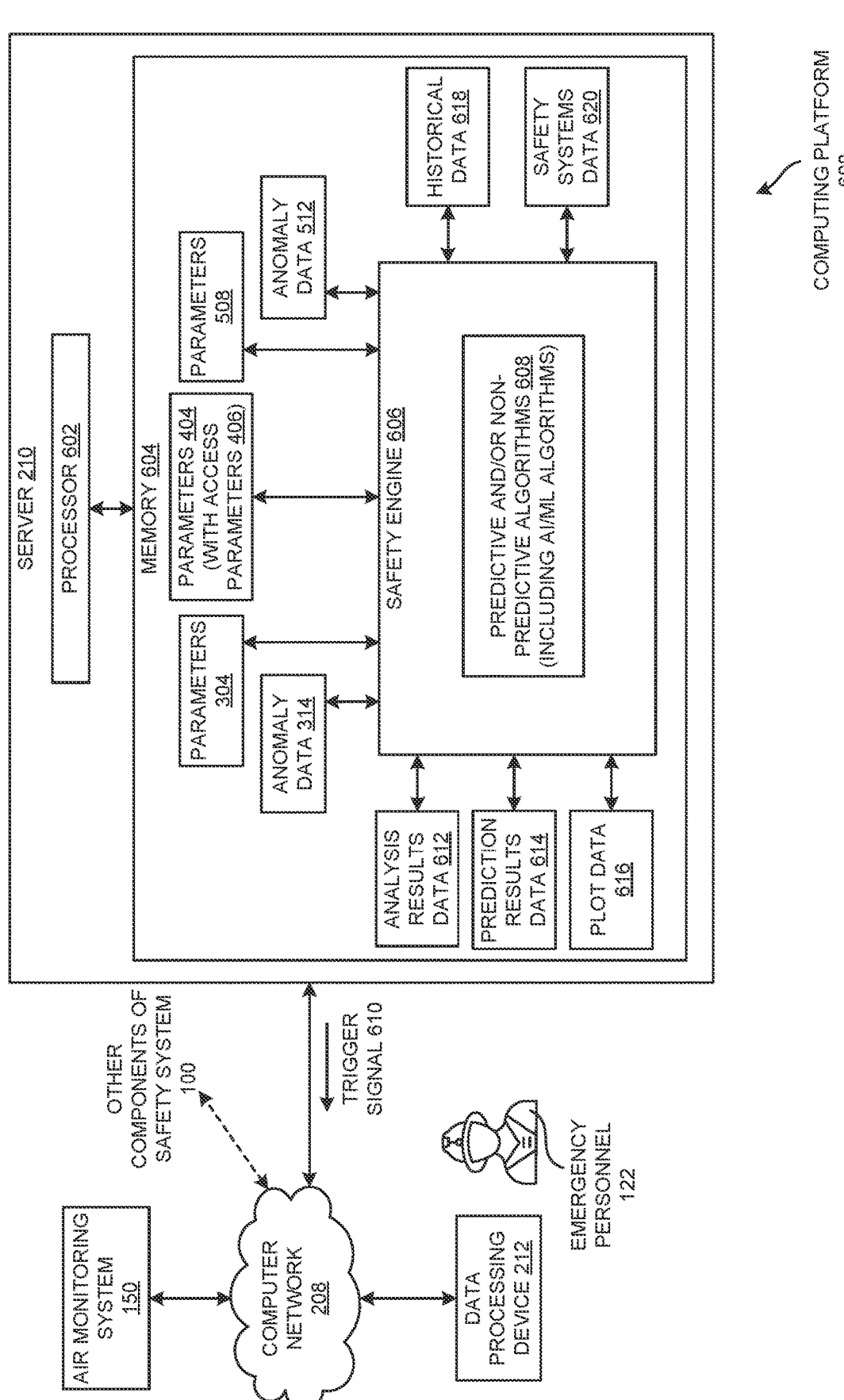
FIG. 6 is a schematic view of a computing platform relevant to the safety system of FIGS. 1-2 implemented through a server, according to one or more embodiments.

FIG. 6 shows a computing platform 600 relevant to the FARS of safety system 100 implemented through server 210, according to one or more embodiments. In one or more embodiments, server 210 may be a distributed (e.g., across a cloud) network of servers, a cluster of servers or a standalone server. As shown in FIG. 6, server 210 may include a processor 602 (e.g., a processor core, a network of processors, a single processor), communicatively coupled to a memory 604 (e.g., a volatile and/or a non-volatile memory). In one or more embodiments, memory 604 may include a safety engine 606 associated with the FARS stored therein and executable through processor 602. FIG. 6 shows memory 604 as including data (e.g., detected, sensed, anomalies) from one or more components of safety system 100; the limited amount of data shown must not be considered as limiting the scope of the exemplary embodiments discussed herein. In one or more embodiments, safety engine 606 may have one or more predictive and/or non-predictive algorithms (e.g., predictive and/or non-predictive algorithms 608) including Artificial Intelligence (AI)/Machine Learning (ML) based algorithms stored therein.

In one or more embodiments, execution of predictive and/or non-predictive algorithms 608 through processor 602 may involve taking the abovementioned data and profiling the FARS implemented as safety system 100. It should be noted that each of the aforementioned data (e.g., parameters 304, parameters 404, access parameters 406, parameters 508, anomaly data 314, anomaly data 512) may be real-time data from elements of safety system 100. In one or more embodiments, analysis of the data may result in beneficial decision making with regard to maintenance of safety system 100, safety of safety system 100 and/or efficiency thereof. For example, anomalies discussed above may be analyzed based on date, time and/or frequency thereof to predict that a specific duration of time in a winter season is associated with diminished characteristics of a component of safety system 100. All possible analyses are within the scope of the exemplary embodiments discussed herein.

In one or more embodiments, server 210 may also be utilized to remotely test and/or trigger operations of one or more components of safety system 100. FIG. 6 shows a trigger signal 610 communicated to air monitoring system 150 to get data thereof discussed above from processor 306, according to one or more embodiments. In some implementations, the components of safety system 100 may automatically transmit data thereof to server 210 and in some others, server 210 may transmit trigger signals (e.g., trigger signal 610) therefor. FIG. 6 also shows results of analysis/prediction through safety engine 606 as analysis results data 612, prediction results data 614 and plot data 616 (e.g., related to graphically plotting the results of analyses). Further, FIG. 6 shows data processing device 212 communicatively coupled to server 210 through computer network 208 as part of computing platform 600, according to one or more embodiments.

Figure 7:
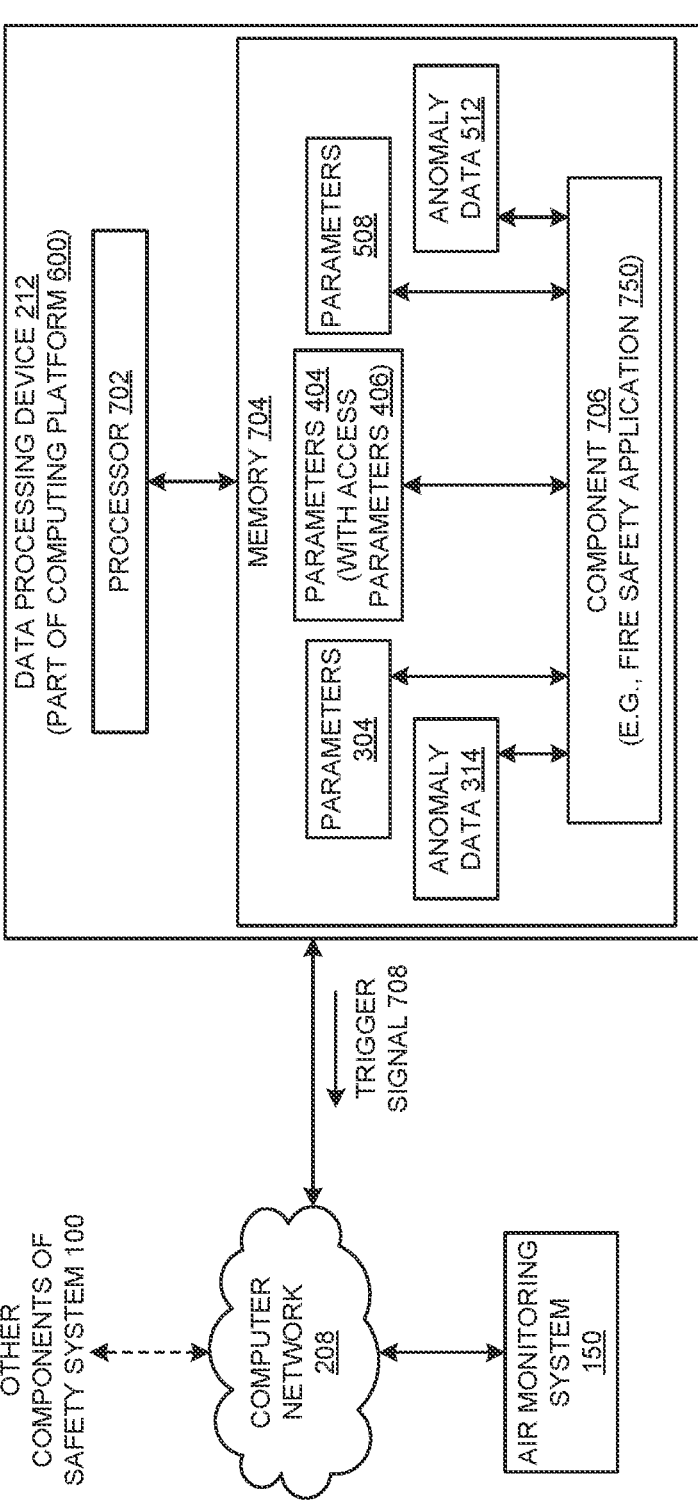
FIG. 7 is a schematic view of a data processing device of FIGS. 2-6, according to one or more embodiments.

FIG. 7 shows data processing device 212 (e.g., a mobile phone, a tablet, a smart device, a laptop) in detail, according to one or more embodiments. In one or more embodiments, again, data processing device 212 may include a processor 702 (e.g., a single processor, a processor core) communicatively coupled to a memory 704 (e.g., a volatile and/or a non-volatile memory). In one or more embodiments, memory 704 may include a component 706 of safety engine 606 stored therein and enabled/provided through processor 602 of server 210. FIG. 7 shows component 706 as a fire safety application 750 merely for example purposes. Again, in one or more embodiments, access to the data of one or more components of safety system 100 may be available to data processing device 212 via component 706 (e.g., through computer network 208 via safety engine 606 of server 210). FIG. 7 also shows capabilities to control components of safety system 100 through data processing device 212 via trigger signals; FIG. 7 specifically shows a trigger signal 708 to initiate collection of data from air monitoring system 150 merely for example purposes. Again, in some implementations, data may be automatically communicated to data processing device 212 and in some others, data processing device 212 may trigger (e.g., through trigger signal 708) collection thereof.

Figure 8:
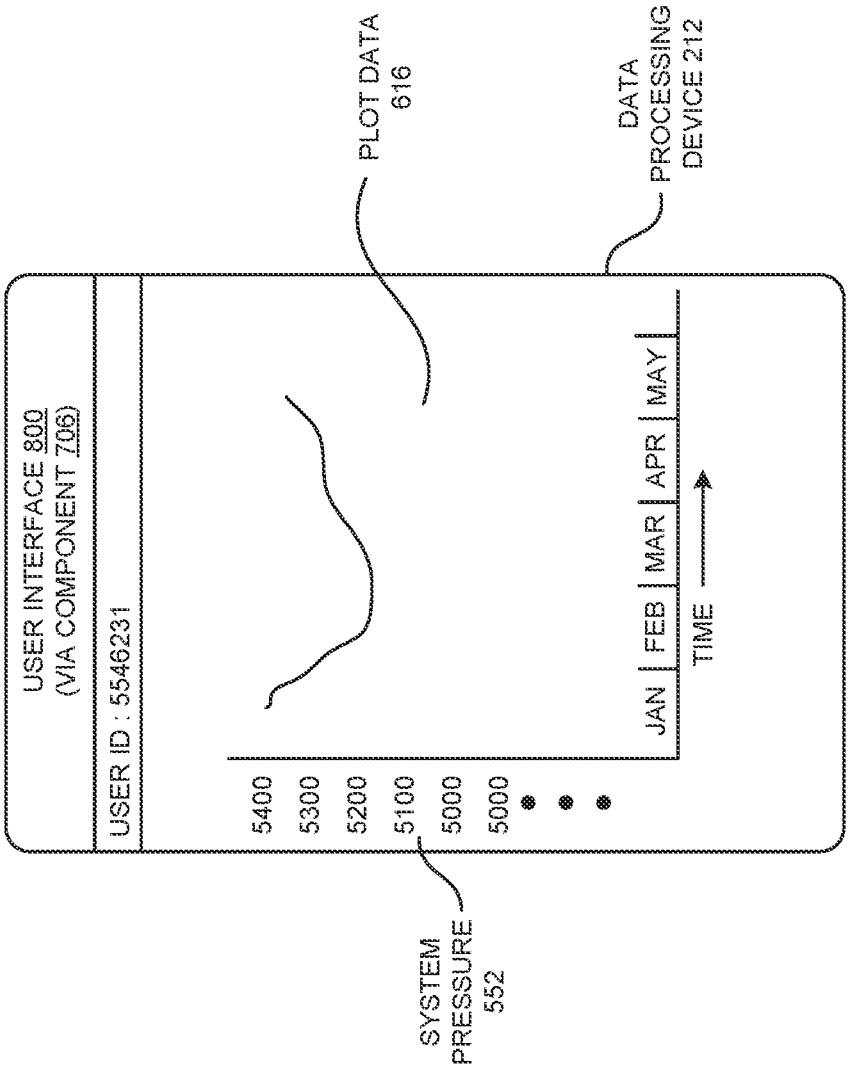
FIG. 8 is an example user interface view of a component of the computing platform of FIG. 6 executing on the data processing device of FIGS. 2-7.

In one or more embodiments, access of emergency air fill station $120_{1-P}$ through component 706 may cause collection of identifier 452 discussed above as part of access parameters 406. FIG. 8 shows an example user interface 800 provided via component 706 (e.g., fire safety application 750) executing on data processing device 212. Here, user interface 800 shows plot data 616 discussed above that may be based on one or more examples of data discussed above and/or analysis results data 612; plot data 616 in FIG. 8 is an evolution of system pressure 552 over a scale of time. Obviously, emergency personnel 122 and/or other users associated with data processing device 212 may access user interface 800 after authentication thereof via computing platform 600 and/or navigating to user interface 800. All reasonable variations are within the scope of the exemplary embodiments discussed herein.

Thus, exemplary embodiments discussed herein provide for an integrated FARS computing platform (e.g., computing platform 600) that enables collection and/or analysis of real-time data from one or more components of safety system 100 and/or control (e.g., remotely; in one scenario, one or more isolation valves $160_{1-P}$ may be opened or closed through server 210/data processing device 212/isolation and bypass control system 202 to control the flow of breathable air 103 from the source thereof to a corresponding one or more emergency air fill stations $120_{1-P}$ in response to collection of air parameters (e.g., parameters 304, parameters 404, parameters 508)) thereof. Further, the integrated FARS computing platform may provide for profiling of safety system 100 and/or emergency personnel 122 and/or remote management of requirements associated with safety system 100. For example, the profiling may involve utilizing (e.g., through safety engine 606) historical data (e.g., historical data 618 stored in memory 604 of server 210) from one or more components of safety system 100 and/or generic safety systems data (e.g., safety systems data 620 stored in memory 604 of server 210) from one or more safety systems other than safety system 100 to arrive at parts of analysis results data 612, prediction results data 614 and/or plot data 616. Again, as discussed above, in one or more embodiments, the integrated FARS computing platform may provide for quick decision making on the part of maintenance personnel, administrative personnel and/or emergency personnel (e.g., emergency personnel 122) associated with safety system 100; statistical analyses and/or data gathering and/or predictive and/or non-predictive analyses may also be enabled through the integrated FARS computing platform.

Also, in one or more embodiments, analogous analyses and/or prediction may also be performed at data processing device 212 based on enablement thereof through component 706. Further, it should be noted that detection of anomalies (e.g., anomaly data 314, anomaly data 512) may be performed through server 210 based on execution of safety engine 606 discussed above instead of or in addition to the detection thereof at the respective components. Last but not the least, as computing platform 600 may be enabled through the execution of safety engine 606, which, in turn, may enable component 706, both safety engine 606 and component 706 may be interpreted as computing platform 600 executing on server 210 and data processing device 212 respectively. All reasonable variations are within the scope of the exemplary embodiments discussed herein.

FIG. 9 shows a process flow diagram detailing the operations involved in realizing a sensor integrated computing platform (e.g., computing platform 600, safety engine 606, component 706) of a safety system (e.g., safety system 100) of a structure (e.g., structure 102) for remote control and access thereof, according to one or more embodiments. In one or more embodiments, operation 902 may involve executing the computing platform on a data processing device (e.g., server 210, data processing device 212). In one or more embodiments, operation 904 may involve integrating the computing platform with a set of sensors (e.g., air parameter sensors $302_{1-R}$, environment sensors $402_{1-B}$, sensors $506_{1-C}$ associated with a number of components (e.g., air monitoring system 150, emergency air fill station $120_{1-P}$, air storage system 106) of the safety system.

In one or more embodiments, operation 906 may then involve, in accordance with the execution of the computing platform on the data processing device and the integration thereof with the set of sensors, through the data processing device, collecting a number of parameters (e.g., parameters 304, parameters 404, parameters 508) of the number of components of the safety system and/or of access (e.g., access parameters 406) thereof through detection of the number of parameters via the set of sensors. In one or more embodiments, the number of parameters may include one or more parameter(s) (e.g., system pressure 552, leakage 554, output flow rate 556, fill pressures 460) related to breathable air (e.g., breathable air 103) from a source (e.g., air storage system 106) within the safety system supplied thereacross via a fixed piping system (e.g., fixed piping system 104) implemented therein and/or access of the breathable air.

In one or more embodiments, operation 906 may also involve monitoring the safety system and/or one or more component(s) of the number of components thereof based on the collected number of parameters.

Although the present embodiments have been described with reference to specific example embodiments, it will be evident that various modifications and changes may be made to these embodiments without departing from the broader spirit and scope of the various embodiments.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

What is claimed is:

1. A method of a safety system of a structure having a fixed piping system implemented therein to supply breathable air from a source across the safety system, comprising:
executing a computing platform on a data processing device;
integrating the computing platform with a set of sensors associated with a plurality of components of the safety system; and
in accordance with the execution of the computing platform on the data processing device and the integration thereof with the set of sensors, through the data processing device, collecting a plurality of parameters at least one of: of the plurality of components of the safety system and of access thereof through detection of the plurality of parameters via the set of sensors, the plurality of parameters comprising at least one parameter related to one or more of the breathable air, access of the breathable air, and access parameters including personnel identification, time of access to the breathable air, and frequency of access to the breathable air; and
monitoring at least one of: the safety system and at least one component of the plurality of components thereof based on the collected plurality of parameters.

2. The method of claim 1, comprising the data processing device being a server remote from the safety system of the structure, the server being one of: a standalone server, a distributed network of servers and a cluster of servers.

3. The method of claim 1, comprising the computing platform being a component of another computing platform executing on a server communicatively coupled to the data processing device.

4. The method of claim 1, wherein monitoring the at least one of: the safety system and the at least one component through the data processing device comprises at least one of:
predictively and non-predictively analyzing the plurality of parameters collected; and
profiling the safety system in accordance with the at least one of: the predictive and the non-predictive analysis of the plurality of parameters collected.

5. The method of claim 1, further comprising at least one of:
collecting at least one anomaly in the plurality of parameters based on detecting, at least one of: through the data processing device and at least one sensor of the set of sensors, that a corresponding at least one parameter of the plurality of parameters is outside a predetermined threshold; and
triggering the collection of the plurality of parameters via a user interface provided through the computing platform executing on the data processing device.

6. The method of claim 3, comprising the component being an application executing on the data processing device.

7. The method of claim 1, further comprising, in accordance with the executing of the computing platform on the data processing device, one of: opening and closing at least one valve in the safety system to control a flow of the breathable air from the source to at least one emergency air fill station within the safety system in response to collecting the plurality of parameters.

8. The method of claim 1, comprising the at least one component of the plurality of components of the safety system being Internet of Things (IoT) enabled.

9. A data processing device of a safety system of a structure having a fixed piping system implemented therein to supply breathable air from a source across the safety system, comprising:
a memory comprising instructions associated with a computing platform stored therein; and
a processor communicatively coupled to the memory, the processor executing the instructions associated with the computing platform to:
integrate the computing platform with a set of sensors associated with a plurality of components of the safety system,
in accordance with the integration, collect a plurality of parameters at least one of: of the plurality of components of the safety system and of access thereof through detection of the plurality of parameters via the set of sensors, the plurality of parameters comprising at least one parameter related to one or more of the breathable air, access of the breathable air, and access parameters including personnel identification, time of access to the breathable air, and frequency of access to the breathable air, and
monitor at least one of: the safety system and at least one component of the plurality of components thereof based on the collected plurality of parameters.

10. The data processing device of claim 9, wherein the data processing device is a server remote from the safety system of the structure, the server being one of: a standalone server, a distributed network of servers and a cluster of servers.

11. The data processing device of claim 9, wherein the processor executes the instructions associated with the computing platform to monitor the at least one of: the safety system and the at least one component based on at least one of:

at least one of: predictively and non-predictively analyzing the plurality of parameters collected, and profiling the safety system in accordance with the at least one of: the predictive and the non-predictive analysis of the plurality of parameters collected.

12. The data processing device of claim 9, wherein the processor further executes instructions associated with the computing platform to collect at least one anomaly in the plurality of parameters based on detecting, in conjunction with at least one sensor of the set of sensors, that a corresponding at least one parameter of the plurality of parameters is outside a predetermined threshold.

13. A safety system of a structure having a fixed piping system implemented therein to supply breathable air from a source across the safety system, comprising:

a data processing device executing a computing platform thereon; and a set of sensors associated with a plurality of components of the safety system, wherein the execution of the computing platform on the data processing device integrates the computing platform with the set of sensors associated with the plurality of components of the safety system, and wherein, in accordance with the execution of the computing platform on the data processing device and the integration thereof with the set of sensors, the data processing device:

collects a plurality of parameters at least one of: of the plurality of components of the safety system and of access thereof through detection of the plurality of parameters via the set of sensors, the plurality of parameters comprising at least one parameter related to one or more of the breathable air, access of the breathable air, and access parameters including personnel identification, time of access to the breathable air, and frequency of access to the breathable air, and monitors at least one of: the safety system and at least one component of the plurality of components thereof based on the collected plurality of parameters.

14. The safety system of claim 13, wherein the data processing device is a server remote from the safety system of the structure, the server being one of: a standalone server, a distributed network of servers and a cluster of servers.

15. The safety system of claim 13, wherein the computing platform is a component of another computing platform executing on a server communicatively coupled to the data processing device.

16. The safety system of claim 13, wherein the data processing device executes the computing platform to monitor the at least one of: the safety system and the at least one component based on at least one of:

at least one of: predictively and non-predictively analyzing the plurality of parameters collected, and profiling the safety system in accordance with the at least one of: the predictive and the non-predictive analysis of the plurality of parameters collected.

17. The safety system of claim 13, wherein at least one of:

the data processing device further executes the computing platform to collect at least one anomaly in the plurality of parameters based on detecting, at least one of: through the data processing device and at least one sensor of the set of sensors, that a corresponding at least one parameter of the plurality of parameters is outside a predetermined threshold, and the computing platform executing on the data processing device provides a user interface to trigger the collection of the plurality of parameters therethrough.

18. The safety system of claim 15, wherein the component is an application executing on the data processing device.

19. The safety system of claim 13, wherein the data processing device executes the computing platform to one of: open and close at least one valve in the safety system to control a flow of the breathable air from the source to at least one emergency air fill station within the safety system in response to the collection of the plurality of parameters.

20. The safety system of claim 13, wherein the at least one component of the plurality of components of the safety system is IoT enabled.

* * * * *